US011832987B2

(12) United States Patent
Hyun et al.

(10) Patent No.: US 11,832,987 B2
(45) Date of Patent: Dec. 5, 2023

(54) ULTRASOUND IMAGING APPARATUS AND OPERATION METHOD THEREFOR

(71) Applicant: SAMSUNG MEDISON CO., LTD., Hongcheon-gun (KR)

(72) Inventors: Dong-gyu Hyun, Hongcheon-gun (KR); Chil-su Kim, Hongcheon-gun (KR); Ki-sang Yoon, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 1173 days.

(21) Appl. No.: 16/096,350

(22) PCT Filed: Apr. 3, 2017

(86) PCT No.: PCT/KR2017/003629
§ 371 (c)(1),
(2) Date: Oct. 25, 2018

(87) PCT Pub. No.: WO2017/195982
PCT Pub. Date: Nov. 16, 2017

(65) Prior Publication Data
US 2019/0125294 A1 May 2, 2019

(30) Foreign Application Priority Data
May 10, 2016 (KR) .................. 10-2016-0057133

(51) Int. Cl.
*A61B 8/08* (2006.01)
*A61B 8/06* (2006.01)
*A61B 8/00* (2006.01)

(52) U.S. Cl.
CPC .................. *A61B 8/06* (2013.01); *A61B 8/08* (2013.01); *A61B 8/461* (2013.01); *A61B 8/488* (2013.01); *A61B 8/0866* (2013.01)

(58) Field of Classification Search
CPC .. A61B 8/06; A61B 8/08; A61B 8/488; A61B 8/0866
See application file for complete search history.

(56) References Cited

U.S. PATENT DOCUMENTS 4,913,159 A * 4/1990 Gardin .................. A61B 8/06
600/456
6,019,723 A * 2/2000 Yamaura .............. A61B 8/0866
600/443

(Continued)

FOREIGN PATENT DOCUMENTS

JP 2006-247206 A 9/2006
JP 2007-504883 A 3/2007

(Continued)

OTHER PUBLICATIONS

Azpurua et al, Acceleration/ejection time ratio in the fetal pulmonary artery predicts fetal lung maturity, Jul. 2010, American Journal of Obstetrics and Gynecology, 203, p. 40.e1-40.e8 (Year: 2010).*

(Continued)

*Primary Examiner* — Rochelle D Turchen
(74) *Attorney, Agent, or Firm* — Sughrue Mion, PLLC

(57) ABSTRACT

An ultrasound imaging apparatus includes a probe configured to receive ultrasound data from a lung of a fetus; a processor configured to obtain Doppler data based on the ultrasound data, to measure a value about at least one parameter used to estimate lung maturity of the fetus, and to estimate the fetal lung maturity by using the measured value about at least one parameter; and a display configured to display a result of estimated lung maturity.

8 Claims, 25 Drawing Sheets

(56) References Cited

U.S. PATENT DOCUMENTS

| | | | |
|---|---|---|---|
| 2007/0081705 A1* | 4/2007 | Carneiro | G06F 18/2321 382/128 |
| 2012/0184830 A1 | 7/2012 | Balberg et al. | |

FOREIGN PATENT DOCUMENTS

| | | | |
|---|---|---|---|
| JP | 2008-183063 A | 8/2008 | |
| JP | 2009-261800 A | 11/2009 | |
| JP | 2011-156251 A | 8/2011 | |
| JP | 2013-17689 A | 1/2013 | |
| JP | 2013-123582 A | 6/2013 | |
| JP | 2014-124269 A | 7/2014 | |
| KR | 10-2010-0084717 A | 7/2010 | |
| KR | 10-2015-0047333 A | 5/2015 | |
| WO | 2005/025399 A2 | 3/2005 | |
| WO | 2014/124253 A2 | 8/2014 | |
| WO | WO-2015105195 A1 * | 7/2015 | A61K 31/519 |

OTHER PUBLICATIONS

Montse Palacio et al., Performance of an automatic quantitative ultrasound analysis of the fetal lung to predict fetal lung maturity, Oct. 1, 2012, American Journal of Obstetrics and Gynecology, 504.e1-504.e5 (Year: 2012).*

Communication dated Jan. 15, 2020, from the European Patent Office in counterpart European Application No. 17796282.6.

Humberto Azpurua et al. "Acceleration/ejection time ratio in the fetal pulmonary artery predicts fetal lung maturity" American Journal of Obstetrics & Gynecology, vol. 203, No. 1, Jul. 1, 2020, (8 pages total) XP027109411.

Shinji Fuke et al. "Antenatar prediction of pulmonary hypoplasia by acceleration time/ejection time ratio of fetal pulmonary arteries by Doppler blood flow velocimetry" Obstetrics and Gynecology, Jan. 1, 2002, (pp. 228-233) XP055654750.

A. Whitehouse et al. "Computer-Based Statistical Pattern Recognition of Doppler Spectral Waveform Kinematics During Fetal respiration" IEEE, Apr. 6, 2006, (pp. 880-883) XP010912928.

Shuichiro Yoshimura et al. "Diagnosis of fetal pulmonary bypoplasia by measurements of blood flow velocity waveforms of pulmoary arteries with Doppler ultrasonography" American Journal of Obstetrics & Gynecology, vol. 180, No. 2, Feb. 1, 1999, (pp. 441-446) XP005690581.

J. A. M. Laudy et al. "Doppler ultrasound imaging: a new technique to detect lung hypoplasia before birth" Ultrasound Obstet. Gynecol. vol. 7, Jan. 1, 1996, (pp. 189-192) XP 055654752.

K. N. Bhanu Prakash et al., "Fetal Lung Maturity Analysis Using Ultrasound Image Features", IEEE Transactions on Information Technology in Biomedicine, vol. 6, No. 1, IEEE, Mar. 2002, pp. 38-45.

Mohamed Ahmed Bahaa Eldin Mohamed et al., "Acceleration/ Ejection Time Ratio in the Fetal Pulmonary Artery Predicts Fetal Lung Maturity in Diabetic Pregnancies", International Journal of Obstetrics and Gynaecology Research (IJOGR), vol. 2, No. 1, Feb. 22, 2015, 12 pages.

International Search Report (PCT/ISA/210) and Written Opinion (PCT/ISA/237) dated Jul. 28, 2017 issued by the International Searching Authority in International Application No. PCT/KR2017/ 003629.

* cited by examiner

| | ... | 100 | 110 | 120 | 130 | ... |
|---|---|---|---|---|---|---|
| ... | ... | ... | ... | ... | ... | ... |
| 200 | ... | 24w2d ±3d | 24w2d ±3d | 24w3d ±3d | 24w3d ±4d | ... |
| 210 | ... | 24w3d ±3d | 24w4d ±3d | 24w4d ±3d | 24w4d ±4d | ... |
| 220 | ... | 24w4d ±3d | 24w5d ±3d | 25w0d ±3d | 25w0d ±1d | ... |
| ... | ... | ... | ... | ... | ... | ... |

1720

ULTRASOUND IMAGING APPARATUS AND OPERATION METHOD THEREFOR

TECHNICAL FIELD

One or more embodiments relate to an ultrasound imaging apparatus and a method of operating the ultrasound imaging apparatus.

BACKGROUND ART

Ultrasound diagnosis apparatuses transmit ultrasound signals generated by transducers of a probe to an object and receive echo signals reflected from the object, thereby obtaining at least one image of an internal part of the object.

In particular, ultrasound diagnosis apparatuses are used for medical purposes including observation of the interior of an object, detection of foreign substances, and diagnosis of damage to the object.

Such ultrasound diagnosis apparatuses provide high stability, display images in real time, and are safe due to the lack of radioactive exposure, compared to X-ray apparatuses. Therefore, ultrasound imaging apparatuses are widely used together with other image diagnosis apparatuses.

DISCLOSURE

Technical Solution

One or more embodiments include an ultrasound imaging apparatus capable of measuring lung maturity of a fetus by using Doppler data and displaying a measurement result.

One or more embodiments include an ultrasound imaging apparatus capable of improving time accuracy of Doppler data obtained from a Doppler image.

One or more embodiments include a non-transitory computer-readable recording medium having embodied thereon a program for executing a method of operating the ultrasound imaging apparatus.

Additional aspects will be set forth in part in the description which follows and, in part, will be apparent from the description, or may be learned by practice of the presented embodiments.

According to one or more embodiments, an ultrasound imaging apparatus includes a probe configured to receive ultrasound data from a lung of a fetus; a processor configured to obtain Doppler data based on the ultrasound data, to measure a value about at least one parameter used to estimate lung maturity of the fetus, and to estimate the fetal lung maturity by using the measured value about at least one parameter; and a display configured to display a result of estimated lung maturity.

The at least one parameter is a parameter related to a pulmonary blood flow index of the fetus.

The at least one parameter includes: an acceleration time representing a time period from a reference time point to a point when a blood flow rate in the pulmonary trunk of the fetus according to contraction of the heart of the fetus; and an ejection time representing a time period from the reference time point to a point when the blood flow rate in the pulmonary trunk of the fetus according to relaxation of the heart of the fetus, wherein the processor automatically calculates values about the acceleration time and the ejection time based on the Doppler data to estimate the fetal lung maturity.

The Doppler data is a Doppler waveform having periods and representing the blood flow rate in the pulmonary trunk of the fetus.

The processor estimates the fetal lung maturity by using the measured value about at least one parameter and a standard value about the at least one parameter of a plurality of fetuses according to gestation growth.

The processor compares the measured value about the at least one parameter with the standard value, and estimates gestation of the fetal lung maturity according to a comparison result.

The display displays at least one of the estimated gestation of the fetal lung maturity and an index representing the estimated gestation of the fetal lung maturity.

The display displays the measured value about the at least one parameter and the standard value of the at least one parameter according to the estimated gestation of the fetal lung maturity.

The display displays the Doppler image obtained from the ultrasound data and actual gestation of the fetal lung maturity.

The display displays the estimated gestation of the fetal lung maturity and the actual gestation of the fetal lung maturity on a graph to be distinguished from each other.

The processor determines safety of the fetal lung maturity based on at least one of the estimated gestation of the fetal lung maturity according to the gestation growth of the fetus and the index representing the estimated gestation of the fetal lung maturity, and the display displays a result of determination of the safety of the fetal lung maturity. The Doppler data is a color Doppler image.

The ultrasound imaging apparatus further includes a user interface configured to receive the at least one parameter used to estimate the fetal lung maturity, wherein the processor estimates the fetal lung maturity based on the input at least one parameter.

The user interface receives an input for setting a boundary of a fetal lung area in the Doppler image obtained from the ultrasound data, and the processor determines a size of the fetal lung based on the boundary and estimates the fetal lung maturity by using a standard value about sizes of lungs of a plurality of fetuses according to gestation growth.

According to one or more embodiments, a method of operating an ultrasound imaging apparatus, the method including: obtaining ultrasound data from a lung of a fetus and obtaining Doppler data based on the ultrasound data; measuring a value about at least one parameter used to estimate lung maturity of the fetus based on the Doppler data; estimating the fetal lung maturity by using the measured value about the at least one parameter; and displaying a result of estimating the fetal lung maturity.

According to one or more embodiments, a non-transitory computer-readable recording medium having embodied thereon a program for executing a method of operating an ultrasound imaging apparatus, wherein the method includes: obtaining ultrasound data from a lung of a fetus and obtaining Doppler data based on the ultrasound data; measuring a value about at least one parameter used to estimate lung maturity of the fetus based on the Doppler data; estimating the fetal lung maturity by using the measured value about the at least one parameter; and displaying a result of estimating the fetal lung maturity.

According to one or more embodiments, an ultrasound imaging apparatus including: a probe configured to receive ultrasound data from an object; a processor configured to obtain Doppler data of the object based on the ultrasound data, to set a region of interest of the object in the Doppler image, to obtain Doppler data corresponding to motion having periodicity of the object from the region of interest for a plurality of first sample periods, to obtain an actual period of the motion of the object, and rearrange the Doppler data based on the actual period; and a display configured to display the Doppler image.

The processor arranges the Doppler image corresponding to an actual first period of the object, arranges Doppler data corresponding to an actual second period of the object to overlap with the Doppler data corresponding to the actual first period, and arranges Doppler data corresponding to an actual third period of the object to overlap with the Doppler data corresponding to the actual first period.

The processor obtains Doppler data corresponding to the motion having periodicity of the object for a plurality of second sample periods, and rearranges the Doppler data obtained for the plurality of first sample periods and the Doppler data obtained for the plurality of second sample periods, based on the actual period.

If the actual period is in a multiple relation with the first sample period, the processor sets a second sample period that is not in a multiple relation with the actual period, obtains Doppler data corresponding to the motion of the object from the region of interest for a plurality of second sample periods, and rearranges the Doppler data obtained for the plurality of second sample periods based on the actual period.

The processor obtains the Doppler data by delaying a predetermined period among the plurality of periods.

The processor obtains the actual period of the motion of the object by applying a Fast Fourier Transform to the Doppler data.

The display displays the rearranged Doppler data.

The ultrasound imaging apparatus further includes a user interface configured to receive a user input for setting the region of interest of the object in the Doppler image, wherein the processor obtains Doppler data corresponding to the motion having periodicity of the object based on the user input.

The Doppler image is at least one of a color Doppler image, a power Doppler image, a tissue Doppler image, a vector Doppler image, and a spectral Doppler image.

The object is the heart.

According to one or more embodiments, a method of operating an ultrasound imaging apparatus, the method including: obtaining ultrasound data from an object and obtaining Doppler data of the object based on the ultrasound data; setting a region of interest of the object in a Doppler image, and obtaining the Doppler data corresponding to motion having periodicity of the object from the region of interest for a plurality of first sample periods; obtaining an actual period of the motion of the object based on a frequency analysis of the Doppler data; and rearranging the Doppler data based on the actual period.

According to one or more embodiments, a non-transitory computer-readable recording medium having embodied thereon a program for executing a method of operating an ultrasound imaging apparatus, wherein the method includes: obtaining ultrasound data from an object and obtaining Doppler data of the object based on the ultrasound data; setting a region of interest of the object in a Doppler image, and obtaining the Doppler data corresponding to motion having periodicity of the object from the region of interest for a plurality of first sample periods; obtaining an actual period of the motion of the object based on a frequency analysis of the Doppler data; and rearranging the Doppler data based on the actual period.

DESCRIPTION OF DRAWINGS

These and/or other aspects will become apparent and more readily appreciated from the following description of the embodiments, taken in conjunction with the accompanying drawings in which:

FIG. 8 is a diagram illustrating data determining an estimated lung maturity of a fetus based on the acceleration time and the ejection time, according to an embodiment;

MODE FOR INVENTION

Figure 1:
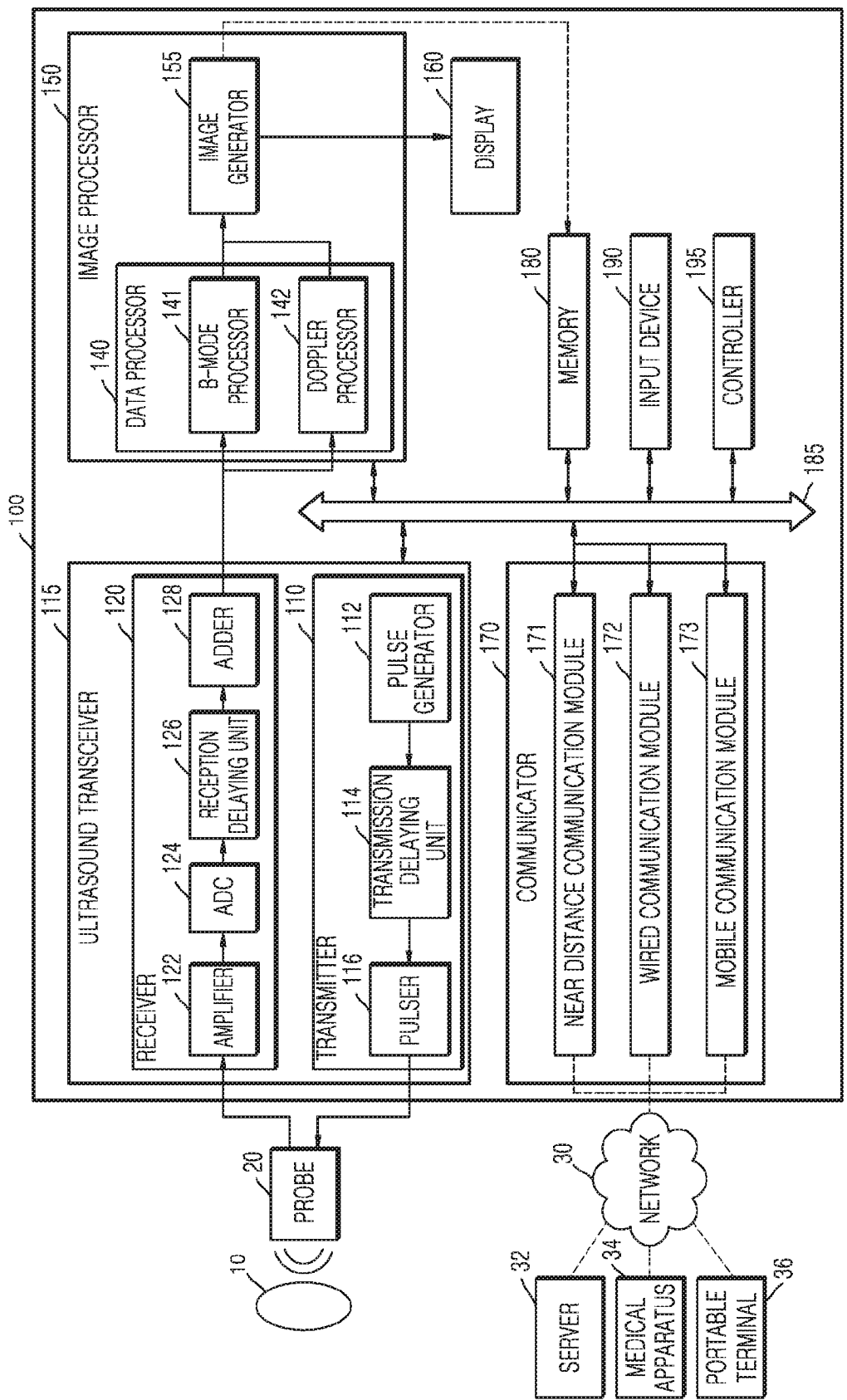
FIG. 1 is a block diagram of an ultrasound diagnosis apparatus according to an embodiment.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the invention.

When a part "includes" or "comprises" an element, unless there is a particular description contrary thereto, the part can further include other elements, not excluding the other elements. Also, the term "unit" in the specification means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with a smaller number of components and "units", or may be divided into additional components and "units". While such terms as "first," "second," etc., may be used to describe various components, such components are not limited thereto. These terms are used only to distinguish one component from another. For example, a first component may be referred to as a second component without departing from the scope of the inventive concept, and similarly, a second component may be referred to as a first component. As used herein, the term "and/or" includes any and all combinations of one or more of the associated listed items. Expressions such as "at least one of," when preceding a list of elements, modify the entire list of elements and do not modify the individual elements of the list. In the present specification, an "image" may refer to multi-dimensional data composed of discrete image elements (e.g., pixels in a two-dimensional (2D) image and voxels in a three-dimensional (3D) image).

Throughout the specification, an "ultrasound image" refers to an image of an object, which is obtained using ultrasound waves. An ultrasound image may denote an image obtained by irradiating an ultrasound signal generated from a transducer of a probe to an object, and receiving information of an echo signal reflected by the object. Also, the ultrasound image may be variously implemented, and for example, the ultrasound image may be at least one of an amplitude (A) mode image, a brightness (B) mode image, a color (C) mode image, and a Doppler (D) mode image. Also, the ultrasound image may be a two-dimensional (2D) image or a three-dimensional (3D) image. Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism.

Throughout the specification, a "user" may be, but is not limited to, a medical expert, for example, a medical doctor, a nurse, a medical laboratory technologist, or a medical imaging expert, or a technician who repairs medical apparatuses.

Reference will now be made in detail to embodiments, examples of which are illustrated in the accompanying drawings. In this regard, the present embodiments may have different forms and should not be construed as being limited to the descriptions set forth herein.

FIG. 1 is a block diagram showing a configuration of an ultrasound diagnosis apparatus 100 according to an embodiment.

Referring to FIG. 1, the ultrasound diagnosis apparatus 100 may include a probe 20, an ultrasound transceiver 115, an image processor 150, a display 160, a communication module 170, a memory 180, a user input unit 190, and a controller 195. Also, the above-mentioned components may be connected with each other via a bus 185, and the image processor 150 may include an image generator 155, a cross-section information detector (not shown), and the display 160.

A person of ordinary skill in the art will understand that other general purpose components besides the components illustrated in FIG. 1 may be further included.

In some embodiments, the ultrasound diagnosis apparatus 100 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 100 by wire or wirelessly, and according to embodiments, the ultrasound diagnosis apparatus 100 may include a plurality of probes 20.

A transmitter 110 supplies a driving signal to the probe 20. The transmitter 110 includes a pulse generator 112, a transmission delaying unit 114, and a pulser 116. The pulse generator 112 generates pulses for forming transmission ultrasound waves based on a predetermined pulse repetition frequency (PRF), and the transmission delaying unit 114 delays the pulses by delay times necessary for determining transmission directionality. The pulses which have been delayed correspond to a plurality of piezoelectric vibrators included in the probe 20, respectively. The pulser 116 applies a driving signal (or a driving pulse) to the probe 20 based on timing corresponding to each of the pulses which have been delayed.

A receiver 120 generates ultrasound data by processing echo signals received from the probe 20. The receiver 120 may include an amplifier 122, an analog-to-digital converter (ADC) 124, a reception delaying unit 126, and a summing unit 128. The amplifier 122 amplifies echo signals in each channel, and the ADC 124 performs analog-to-digital conversion on the amplified echo signals. The reception delaying unit 126 delays digital echo signals output by the ADC 124 by delay times necessary for determining reception directionality, and the summing unit 128 generates ultrasound data by summing the echo signals processed by the reception delaying unit 126.

The image processor 150 generates an ultrasound image by scan-converting ultrasound data generated by the ultrasound transceiver 115.

The ultrasound image may be not only a grayscale ultrasound image obtained by scanning an object in an amplitude (A) mode, a brightness (B) mode, and a motion (M) mode, but also may represent motion of an object by using a Doppler image. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 141 extracts B mode components from ultrasound data and processes the B mode components. The image generator 155 may generate an ultrasound image indicating signal intensities as brightness based on the extracted B mode components.

Similarly, a Doppler processor 142 may extract Doppler components from ultrasound data, and the image generator 155 may generate a Doppler image indicating a movement of an object as colors or waveforms based on the extracted Doppler components.

The image generator 155 may generate a 2D ultrasound image or a 3D ultrasound image of an object, and may also generate an elastic image that shows a degree of deformation of an object 10 depending on pressure. Furthermore, the image generator 155 may display various pieces of additional information in an ultrasound image by using text and graphics. In addition, the generated ultrasound image may be stored in the memory 180.

The display 160 displays the generated ultrasound image. The display 160 may display not only an ultrasound image, but also various pieces of information processed by the ultrasound diagnosis apparatus 100 on a screen image via a graphical user interface (GUI). In addition, the ultrasound diagnosis apparatus 100 may include two or more displays 160 according to embodiments.

The display 160 may include at least one of a liquid crystal display (LCD), a thin film transistor-liquid crystal display (TFT-LCD), an organic light-emitting diode (OLED) display, a flexible display, a 3D display, and an electrophoretic display.

Also, in the case where the display 160 and a user input unit configure a touchscreen by forming a layered structure, the display 160 may be used as not only an output unit but also an input unit that may receive information via a user's touch.

The touchscreen may be configured to detect even touch pressure as well as a touch location and a touched area. Also, the touchscreen may be configured to detect not only a real-touch but also a proximity touch.

In the specification, a "real-touch" denotes a case where a pointer actually touches a screen, and a "proximity-touch" denotes a case where a pointer does not actually touch a screen but is held apart from a screen by a predetermined distance. In the specification, a pointer denotes a touch tool for touching or proximity-touching a specific portion of a displayed screen. For example, a pointer may be an electronic pen, a finger, etc.

Although not shown in the drawings, the ultrasound diagnosis apparatus 100 may include various sensors inside or in the vicinity of a touchscreen in order to detect a direct touch or a proximity touch with respect to the touchscreen.

An example of a sensor for detecting a touch with respect to the touchscreen includes a tactile sensor.

The tactile sensor denotes a sensor for detecting a contact of a specific object to a degree felt by a person or more. The tactile sensor may detect various information such as roughness of a contact surface, hardness of a contact object, and the temperature of a contact point.

Also, an example of a sensor for detecting a touch with respect to the touchscreen includes a proximity sensor. The proximity sensor denotes a sensor for detecting an object approaching a predetermined detection surface or the existence of an object in the neighborhood by using an electromagnetic force or an infrared ray without any mechanical contact.

An example of a proximity sensor includes a transmissive photoelectric sensor, a direct reflective photoelectric sensor, a mirror reflective photoelectric sensor, a high frequency oscillation type proximity sensor, a capacitive proximity sensor, a magnetic proximity sensor, an infrared proximity sensor, etc.

The communication module 170 is connected to a network 30 by wire or wirelessly to communicate with an external device or a server. The communication module 170 may exchange data with a hospital server or another medical apparatus in a hospital, which is connected thereto via a PACS. Furthermore, the communication module 170 may perform data communication according to the digital imaging and communications in medicine (DICOM) standard.

The communication module 170 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 170 may receive information about a diagnosis history or medical treatment schedule of a patient from a server and utilizes the received information to diagnose the patient. Furthermore, the communication module 170 may perform data communication not only with a server or a medical apparatus in a hospital, but also with a portable terminal of a medical doctor or patient.

The communication module 170 is connected to the network 30 by wire or wirelessly to exchange data with a server 32, a medical apparatus 34, or a portable terminal 36. The communication module 170 may include one or more components for communication with external devices. For example, the communication module 1300 may include a local area communication module 171, a wired communication module 172, and a mobile communication module 173.

The local area communication module 171 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 172 refers to a module for communication using electric signals or optical signals. Examples of wired communication techniques according to an embodiment may include communication via a twisted pair cable, a coaxial cable, an optical fiber cable, and an Ethernet cable.

The mobile communication module 173 transmits or receives wireless signals to or from at least one selected from a base station, an external terminal, and a server on a mobile communication network. The wireless signals may be voice call signals, video call signals, or various types of data for transmission and reception of text/multimedia messages.

The memory 180 stores various data processed by the ultrasound diagnosis apparatus 100. For example, the memory 180 may store medical data related to diagnosis of an object, such as ultrasound data and an ultrasound image that are input or output, and may also store algorithms or programs which are to be executed in the ultrasound diagnosis apparatus 100.

The memory 180 may be any of various storage media, e.g., a flash memory, a hard disk drive, EEPROM, etc.

Furthermore, the ultrasound diagnosis apparatus 100 may utilize web storage or a cloud server that performs the storage function of the memory 180 online.

The user input unit 190 generates input data which a user inputs in order to control an operation of the ultrasound diagnosis apparatus 100. The user input unit 190 may include a hardware configuration such as a keypad, a mouse, a touchpad, a track ball, and a jog switch, but is not limited thereto, and may further include various configurations such as an electrocardiogram measurement module, a breathing measurement module, a voice recognition sensor, a gesture recognition sensor, a fingerprint recognition sensor, an iris recognition sensor, a depth sensor, and a distance sensor.

Particularly, the user input unit 190 may also include a touchscreen in which a touchpad and the display 160 form a layered structure.

In this case, the ultrasound diagnosis apparatus 100 according to an embodiment may display an ultrasound image of a predetermined mode and a control panel for an ultrasound image on the touchscreen. Also, the ultrasound diagnosis apparatus 100 may detect a user's touch gesture for an ultrasound image via the touchscreen.

The ultrasound diagnosis apparatus 100 according to an embodiment may physically include some buttons frequently used by a user from among buttons included in a control panel of a general ultrasound apparatus, and provide the rest of the buttons in the form of a GUI via the touchscreen.

The controller 195 may control all operations of the ultrasound diagnosis apparatus 100. In other words, the controller 195 may control operations among the probe 20, the ultrasound transceiver 115, the image processor 150, the communication module 170, the memory 180, and the user input unit 190 shown in FIG. 1.

All or some of the probe 20, the ultrasound transceiver 115, the image processor 150, the communication module 170, the memory 180, the user input unit 190, and the controller 195 may be implemented as software modules. However, embodiments of the present invention are not limited thereto, and some of the components stated above may be implemented as hardware modules. Furthermore, at least one selected from the ultrasound transceiver 115, the image processor 150, and the communication module 170 may be included in the controller 195. However, embodiments of the present invention are not limited thereto.

Figure 2:
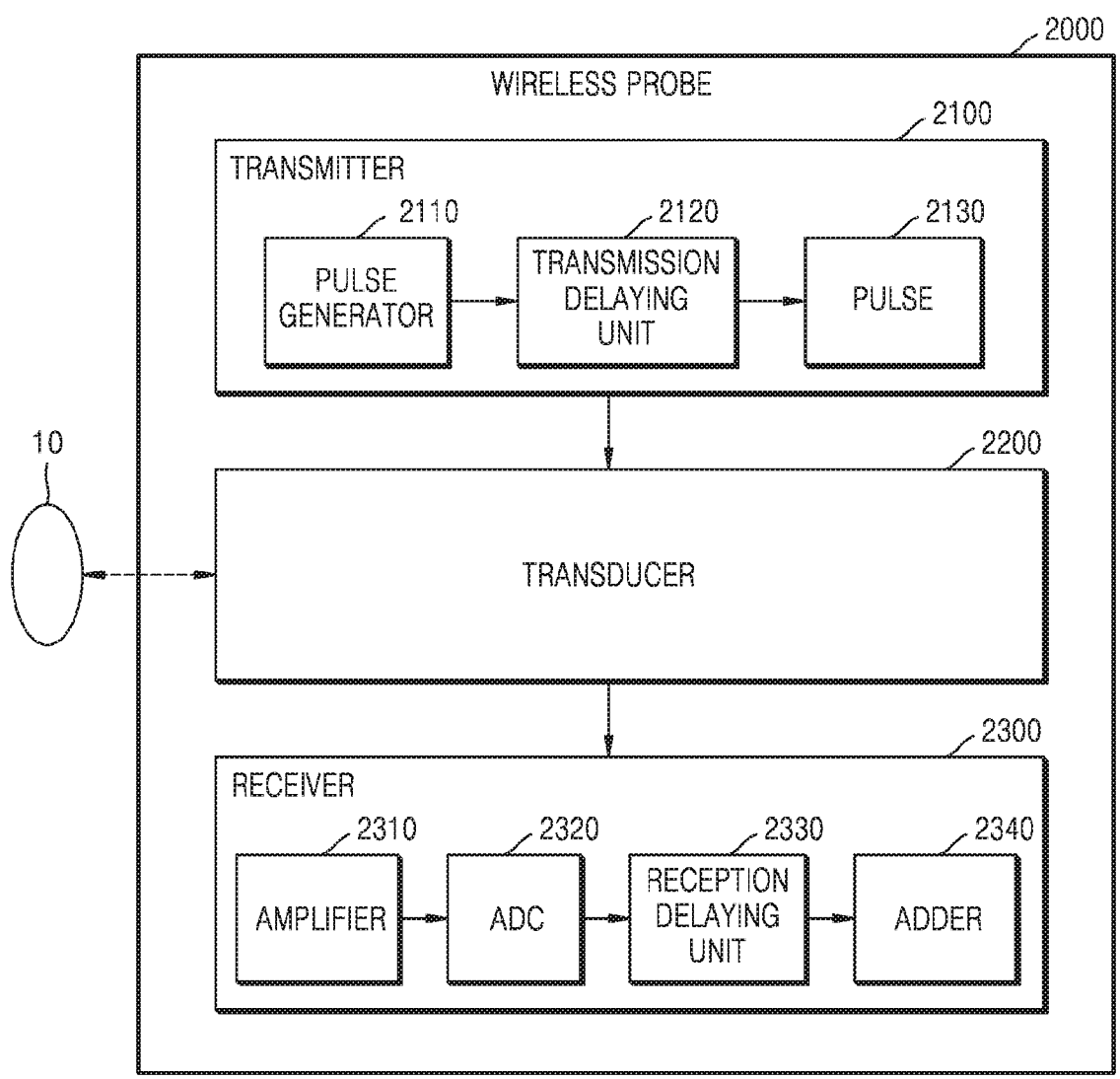
FIG. 2 is a block diagram of a wireless probe according to an embodiment.

FIG. 2 is a block diagram showing a configuration of a wireless probe 2000 according to an embodiment. As described above with reference to FIG. 1, the wireless probe 2000 may include a plurality of transducers, and, according to embodiments, may include some or all of the components of the ultrasound diagnosis apparatus 100 shown in FIG. 1.

The wireless probe 2000 according to the embodiment shown in FIG. 2 includes a transmitter 2100, a transducer 2200, and a receiver 2300. Since descriptions thereof are given above with reference to FIG. 1, detailed descriptions thereof will be omitted here. In addition, according to embodiments, the wireless probe 2000 may selectively include a reception delaying unit 2330 and a summing unit 2340.

The wireless probe 2000 may transmit ultrasound signals to the object 10, receive echo signals from the object 10, generate ultrasound data, and wirelessly transmit the ultrasound data to the ultrasound diagnosis apparatus 100 shown in FIG. 1.

The wireless probe 2000 may be a smart apparatus that may perform ultrasound scanning by including a transducer array. Specifically, the wireless probe 2000 is a smart apparatus, scans an object by using a transducer array, and obtains ultrasound data. Then, the wireless probe 2000 may generate and/or display an ultrasound image by using the obtained ultrasound data. The wireless probe 2000 may include a display, and display a screen including a user interface screen for controlling at least one ultrasound image and/or a scan operation of an object via the display.

While a user scans a patient's predetermined body portion, which is an object, by using the wireless probe 2000, the wireless probe 2000 and the ultrasound diagnosis apparatus 100 may continue to transmit/receive predetermined data via a wireless network. Specifically, while a user scans a patient's predetermined body portion, which is an object, by using the wireless probe 2000, the wireless probe 2000 may transmit ultrasound data to the ultrasound diagnosis apparatus 100 in real-time via the wireless network. The ultrasound data may be updated in real-time and transmitted from the wireless probe 2000 to the ultrasound diagnosis apparatus 100 as ultrasound scanning is performed continuously.

Figure 3:
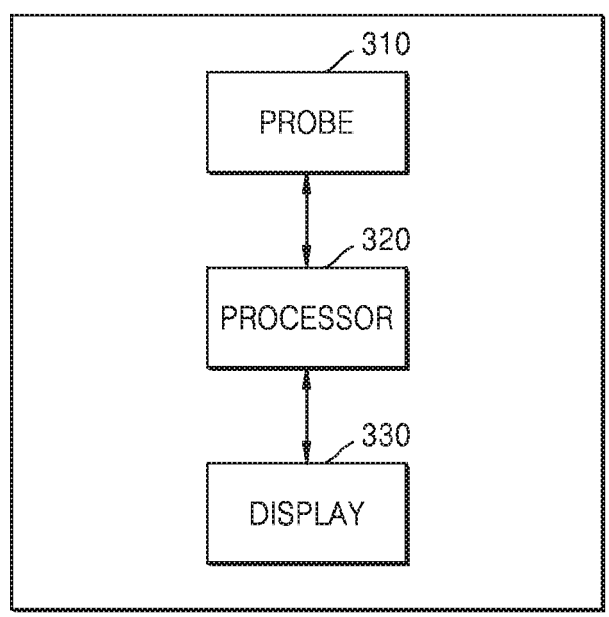
FIG. 3 is a block diagram of an ultrasound imaging apparatus according to an embodiment.

FIG. 3 is a block diagram of an ultrasound imaging apparatus 300 according to an embodiment.

The ultrasound imaging apparatus 300 may include a probe 310, a processor 320, and a display 330. However, not all the elements in FIG. 3 are essential elements. The ultrasound imaging apparatus 300 may include more or less elements than the elements shown in FIG. 3. Hereinafter, the elements will be described below.

The probe 310 may include a plurality of transducers for converting between ultrasound signals and electric signals. That is, the probe 310 may include a transducer array including a plurality of transducers, and the plurality of transducers may be arranged one-dimensionally or two-dimensionally. Each of the plurality of transducers may separately generate an ultrasound signal, and the plurality of transducers may simultaneously generate ultrasound signals. The ultrasound signal transmitted from each of the transducers is reflected by a discontinuous surface of impedance in an object. Each transducer may convert a reflected echo signal into an electric signal. The probe 310 may receive ultrasound data from the lungs of a fetus.

The processor 320 may obtain Doppler data based on the ultrasound data. The Doppler data may be a Doppler wave having periods and representing a blood flow rate in the pulmonary trunk of the fetus. In addition, the Doppler data may be a color Doppler image. One of ordinary skill in the art would appreciate that the Doppler data may include images regarding Doppler, graphs, and values about a certain parameter, but is not limited thereto.

The processor 320 may measure a value about at least one parameter used to estimate lung maturity of the fetus based on the Doppler data.

In the present specification, the "lung maturity" may not only denote simple growth of the lungs of a fetus, but also denote a degree of completion in lung performance so that the fetus is able to respire through the lungs. In addition, the concept of fetal lung maturity may be distinguished from the concept of fetal growth. That is, fetal growth is related to overall growth of the fetus, and fetal lung maturity is regarding whether the lungs of the fetus normally perform, rather than simple growth of the fetus.

Here, the at least one parameter may be a parameter related to an index of pulmonary blood flow of the fetus. In detail, the parameter may include an acceleration time representing a time period from a reference time point to a point when the blood flow rate in the pulmonary trunk of the fetus is the highest, and an ejection time representing a time period from the reference time point to a point when the blood flow rate in the pulmonary trunk of the fetus is changed according to relaxation of the fetal heart. One of ordinary skill in the art would appreciate that one or more embodiments are not limited to the above example of the parameter and the fetal lung maturity may be estimated according to other parameters.

The processor 320 may estimate the fetal lung maturity by using the measured value about at least one parameter. For example, the processor 320 obtains variation in the pulmonary blood flow supplied to the lungs by using the value about the parameter related to the pulmonary blood flow index, and estimates the lung maturity according to the obtained variation in the pulmonary blood flow.

In detail, the processor 320 may estimate the fetal lung maturity by using, for example, the acceleration time and the ejection time. The processor 320 may estimate the fetal lung maturity by using Equation 1 below.

$$\text{lung maturity} = \frac{C \times \text{acceleration time } (AT)}{\text{ejection time } (ET)} \quad (1)$$

Here, C denotes a constant for estimating an index of the lung maturity. The acceleration time and the ejection time are the same as the above description. The processor 320 automatically calculates values regarding the acceleration time and the ejection time based on Doppler data, and estimates the fetal lung maturity.

According to another example, the processor 320 may estimate the fetal lung maturity by using Equation 2 below.

$$\text{lung maturity} = \frac{C \times \text{acceleration time } (AT)/\text{ejection time } (ET)}{\text{representative value}} \quad (2)$$

Here, a representative value is calculated statistically from data about lung maturity according to the gestation growth of a plurality of fetuses. In detail, if actual gestation of the fetus is 23 weeks, the representative value may be a value that is statistically calculated based on fetuses corresponding to 23 weeks among the plurality of fetuses. That is, the processor 320 automatically calculates values regarding the acceleration time and the ejection time based on the Doppler data, and estimates the fetal lung maturity by using the calculated values and the representative value.

As another example, the processor 320 may estimate the fetal lung maturity by using the measured value about at least one parameter and a standard value of a plurality of fetuses about the at least one parameter according to the gestation growth of the fetuses. In detail, the processor 320 compares the measured value with the standard value about the parameter, and estimates the fetal lung maturity according to a comparison result.

The processor 320 may obtain an estimated gestation of lung maturity and an index representing the estimated gestation of lung maturity by using the parameter related to the pulmonary blood flow index. The parameter related to the pulmonary blood flow index may include a peak systolic velocity (PSV), an end diastolic velocity (EDV), a time average mean velocity (TAMV), and a time average peak velocity (TAPV), but is not limited thereto.

In addition, the estimated lung maturity week number index may be generated by combining the above-mentioned parameters. In detail, the index of the estimated gestation of lung maturity may be a ratio between the PSV and the EDV, as expressed by Equations 3 and 4 below.

$$\text{index of estimated gestation of lung maturity} = \frac{\text{peak systolic velocity} | PSV}{\text{end diastolic velocity} | EDV} \quad (3)$$

$$\text{index of estimated gestation of lung maturity} = \frac{\text{peak systolic velocity} | PSV}{\text{end diastolic velocity} | EDV} \quad (4)$$

In addition, the index of the estimated gestation of lung maturity may be generated based on a difference between the PSV and the EDV. This may be expressed by Equation 5 and Equation 6 below.

$$\text{index of estimated gestation of lung maturity} = \frac{PSV - EDV}{PSV} \quad (5)$$

$$\text{index of estimated gestation of lung maturity} = \frac{PSV - EDV}{TAPV} \quad (6)$$

The display 330 displays a predetermined screen. In detail, the display 330 displays a predetermined screen according to control of the processor 320. The display 330 may include a display panel (not shown), and may display a medical image, etc. on the display panel.

The display 330 may represent an estimated result of lung maturity. For example, the display 330 may represent at least one of indexes representing estimated gestation of fetal lung maturity. The display 330 may represent the measured value about the at least one parameter and the standard value about at least one parameter according to the estimated gestation of lung maturity.

In addition, the display 330 may represent the Doppler image obtained from ultrasound data and the actual gestation of fetal lung maturity. In addition, the display 330 may represent the estimated gestation of lung maturity and the actual gestation of fetal lung maturity on a graph to be distinguished from each other.

In addition, the processor 320 may determine safety of the fetal lung maturity, based on at least one of the estimated gestation of the fetal lung maturity and an index representing the estimated gestation of the fetal lung maturity. The display 330 may represent the safety result of the fetal lung maturity.

The ultrasound imaging apparatus 300 includes a central processor that controls all operations of the probe 310, the processor 320, and the display 330. The central processor may be implemented as an array of a plurality of logic gates, or as a combination of a universal microprocessor and a memory storing programs that may be executed in the microprocessor. In addition, one of ordinary skill in the art would appreciate that the central processor may be implemented by other types of hardware.

Figure 4:
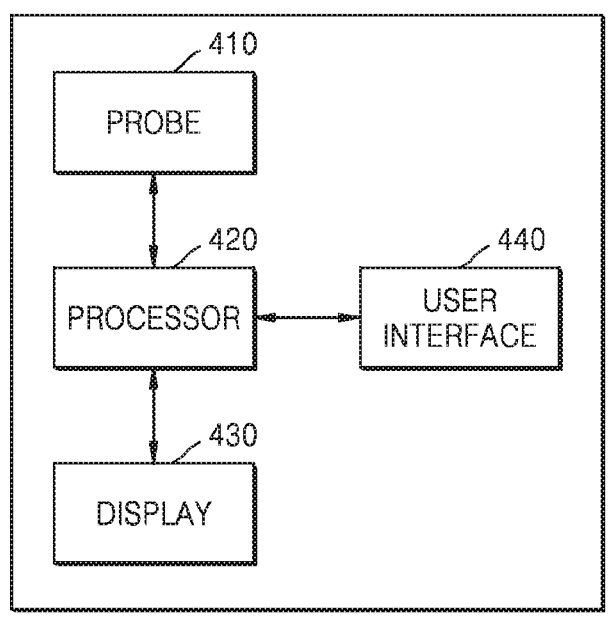
FIG. 4 is a block diagram of an ultrasound imaging apparatus according to another embodiment.

FIG. 4 is a block diagram of an ultrasound imaging apparatus 400 according to another embodiment.

The ultrasound imaging apparatus 400 may include a probe 410, a processor 420, a display 430, and a user interface 440.

In FIG. 4, the probe 410, the processor 420, and the display 430 of the ultrasound imaging apparatus 400 correspond to the probe 310, the processor 320, and the display 330 of the ultrasound imaging apparatus 300 illustrated above with reference to FIG. 3, and thus, detailed descriptions thereof are omitted. The ultrasound imaging apparatus 400 may include more or less elements than the elements shown in FIG. 4. Hereinafter, the elements will be described below.

The user interface 440 is an apparatus for receiving data for controlling the ultrasound imaging apparatus 400 from a user. The processor 420 may control the display 430 to generate and output a user interface screen for receiving a predetermined command or data from the user. The display 430 may display a screen for receiving a parameter that is used to estimate the fetal lung maturity on the display panel.

The user interface 440 may receive the input of at least one parameter used to estimate the fetal lung maturity. The processor 420 may estimate the fetal lung maturity based on the received at least one parameter.

In addition, the user interface 440 may receive an input for setting a boundary of fetal lung area in the Doppler image obtained from the ultrasound data. Here, the user interface 440 may include hardware such as a keypad, a mouse, a touch panel, a touch screen, a track ball, a jog switch, etc., but is not limited thereto. In addition, the user interface 440 may further include various input units such as a voice recognition sensor, a gesture recognition sensor, a fingerprint sensor, an iris sensor, a depth sensor, a distance sensor, etc.

The processor 420 may determine a size of the fetal lung based on the boundary. The processor 420 may estimate the fetal lung maturity by comparing the size of the fetal lung with a standard value of the lung sizes of a plurality of fetuses according to the gestation growth.

In addition, the ultrasound imaging apparatus 400 may further include a storage (not shown) and a communicator (not shown). The storage (not shown) may correspond to the memory 180 of FIG. 1, and the communicator (not shown) may correspond to the communicator 170 of FIG. 1. The storage (not shown) may store data regarding the ultrasound images (e.g., ultrasound images, ultrasound data, scanning data, diagnosis data of a patient, etc.) and data transmitted to the ultrasound imaging apparatus 400 from an external device. The data transmitted from the external device may include information about a patient, data necessary for diagnosing and treating the patient, previous history of the patient, medical work list corresponding to prescription for the patient, etc. The storage (not shown) may store the parameter and the value of the parameter used to estimate the fetal lung maturity. In addition, the storage (not shown) may store standard values of a plurality of fetuses for the parameters according to the gestation growth. The storage (not shown) may store the estimated result of the fetal lung maturity.

The communicator (not shown) may receive/transmit the data from/to the external device. For example, the communicator (not shown) may be connected to a wireless probe or an external device via a communication network according to Wi-Fi or Wi-Fi direct. In detail, a wireless communication network the communicator may access may include wireless LAN, Wi-Fi, Bluetooth, ZigBee, Wi-Fi direct (WFD), ultra wideband (UWB), infrared data association (IrDA), Bluetooth low energy (BLE), and near field communication (NFC), but is not limited thereto.

The ultrasound imaging apparatus 400 includes the central processor for controlling all operations of the probe 410, the processor 420, the display 430, the user interface 440, the storage (not shown), and the communicator (not shown). The central processor may be implemented as an array of a plurality of logic gates, or as a combination of a universal microprocessor and a memory storing programs that may be executed in the microprocessor. In addition, one of ordinary skill in the art would appreciate that the central processor may be implemented by other types of hardware.

Hereinafter, various operations or applications that the ultrasound imaging apparatus 300 or 400 performs will be described. Even when the probe 310 or 410, the processor 320 or 420, the display 330 or 430, the user interface 440, the storage (not shown), and the communicator (not shown) are not specifically described, features that would have been understood or expected by one of ordinary skill in the art may be regarded as their general features. The scope of the present disclosure is not limited to a name or physical/logical structure of a specific component.

Figure 5:
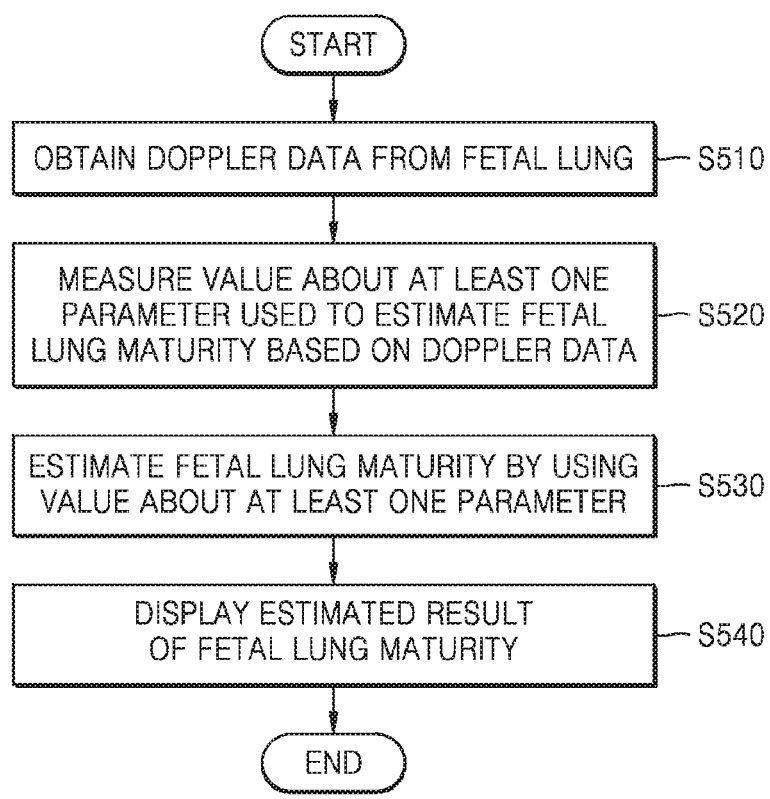
FIG. 5 is a flowchart illustrating a method of operating an ultrasound imaging apparatus, according to an embodiment.

FIG. 5 is a flowchart illustrating a method of operating the ultrasound imaging apparatus 300, according to an embodiment.

Hereinafter, operations of the ultrasound imaging apparatus 300 may be applied to the ultrasound imaging apparatus 400.

In operation S510 of FIG. 5, the ultrasound imaging apparatus 300 obtains ultrasound data from the lungs of a fetus, and obtains Doppler data based on the ultrasound data.

In operation S520, the ultrasound imaging apparatus 300 may measure a value about at least one parameter used to estimate the fetal lung maturity based on the Doppler data. Here, the at least one parameter may be a parameter related to an index of pulmonary blood flow of the fetus. For example, the parameter may include an acceleration time representing a time period from a reference time to a point when the blood flow rate in the pulmonary trunk of the fetus is the highest according to contraction of heart, and an ejection time representing a time period from the reference time to a point when the blood flow rate in the pulmonary trunk of the fetus is changed according to relaxation of heart, but is not limited thereto.

In operation S530, the ultrasound imaging apparatus 300 may estimate the fetal lung maturity by using the measured value about the at least one parameter. In addition, the ultrasound imaging apparatus 300 may determine safety of the fetal lung maturity, based on at least one of the estimated gestation of fetal lung maturity according to gestation growth of the fetus and the index representing the estimated gestation of the fetal lung maturity.

In operation S540, the ultrasound imaging apparatus 300 may display the estimated result of the lung maturity. The ultrasound imaging apparatus 300 may display the measured value about at least one parameter and the standard value about at least one parameter according to the estimated gestation of lung maturity. In addition, the ultrasound imaging apparatus 300 may represent the Doppler image obtained from ultrasound data and the estimated gestation of lung maturity. The ultrasound imaging apparatus 300 may display actual gestation of lung maturity of the fetus. The ultrasound imaging apparatus 300 may represent the estimated gestation of lung maturity and the actual gestation of lung maturity of the fetus on a graph to be distinguished from each other. In addition, the ultrasound imaging apparatus 300 may represent the safety result of the fetal lung maturity.

Figure 6A:
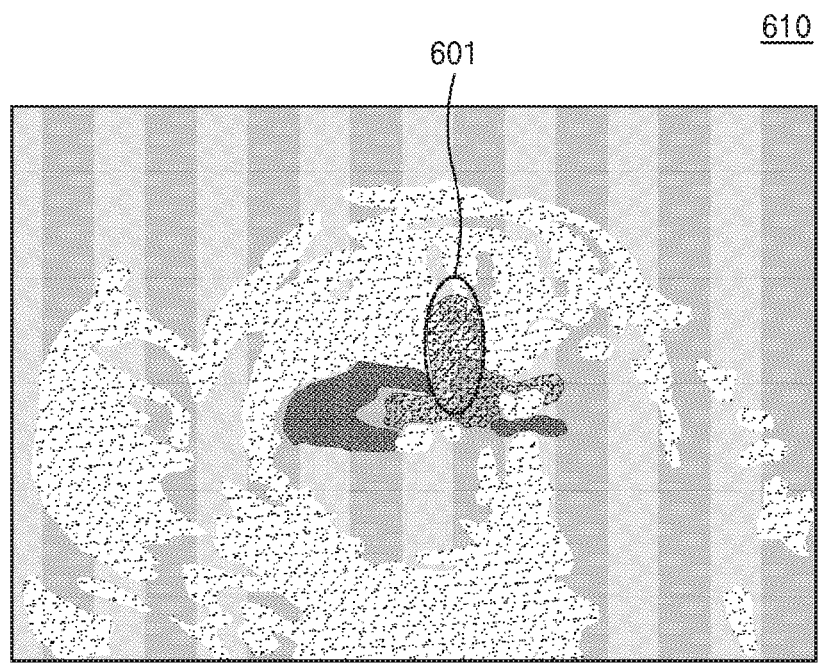
FIG. 6A is a diagram illustrating a Doppler image obtained from a lung of a fetus, according to an embodiment.

FIG. 6A is a diagram illustrating a Doppler image obtained from a lung of a fetus, according to an embodiment.

Referring to FIG. 6A, the ultrasound imaging apparatus 300 may receive ultrasound data from the lung of the fetus, and may generate a Doppler image 610 based on the ultrasound data. The ultrasound imaging apparatus 300 may display the Doppler image 610 on the display screen.

Here, the Doppler image 610 may be at least one of a color Doppler image, a power Doppler image, a tissue Doppler image, a vector Doppler image, and a spectral Doppler image, but is not limited thereto.

The ultrasound imaging apparatus 300 may generate the Doppler image by using a reflected echo signal after transmitting an ultrasound wave to the fetus, or may receive the Doppler image related to the lung of the fetus from an external device that is physically separate from the ultrasound imaging apparatus 300. Here, the external device may be an apparatus for obtaining, storing, processing, or using data related to the ultrasound image, and may be a medical imaging apparatus, a medical server, a portable terminal, or all kinds of computing devices capable of using and processing medical images. For example, the external device may be a medical diagnosis apparatus provided in a medical institute such as a hospital. In addition, the external device may include a server for recording and storing previous medical history of the patient in the hospital, a medical imaging apparatus for a doctor to read the medical images, etc.

Figure 6B:
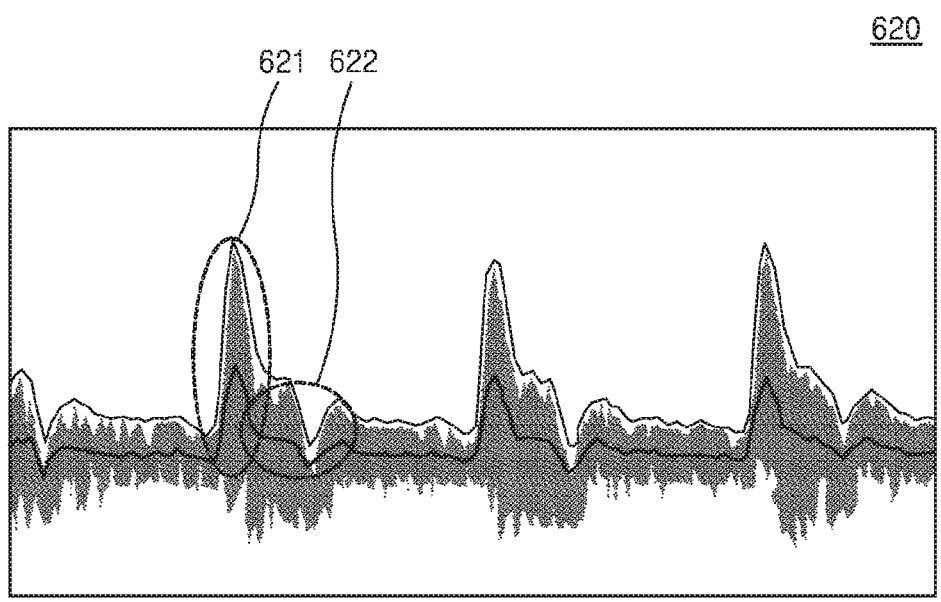
FIG. 6B is a diagram illustrating Doppler data related to a bloodstream in a lung of a fetus, according to another embodiment.

FIG. 6B is a diagram illustrating Doppler data related to a bloodstream in a lung of a fetus, according to another embodiment.

The ultrasound imaging apparatus 300 may obtain Doppler data from the Doppler image corresponding to the lung of the fetus. Here, the Doppler data may be a Doppler waveform 620 having periods and representing the blood flow rate in the pulmonary trunk of the fetus.

Referring to the Doppler waveform 620 shown in the graph of FIG. 6B, a first region 621 is a region of Doppler data corresponding to the blood flow rate in the pulmonary trunk according to the contraction of heart. A second region 622 is a region of Doppler data corresponding to the blood flow rate in the pulmonary trunk according to the relaxation of heart.

Figure 7A:
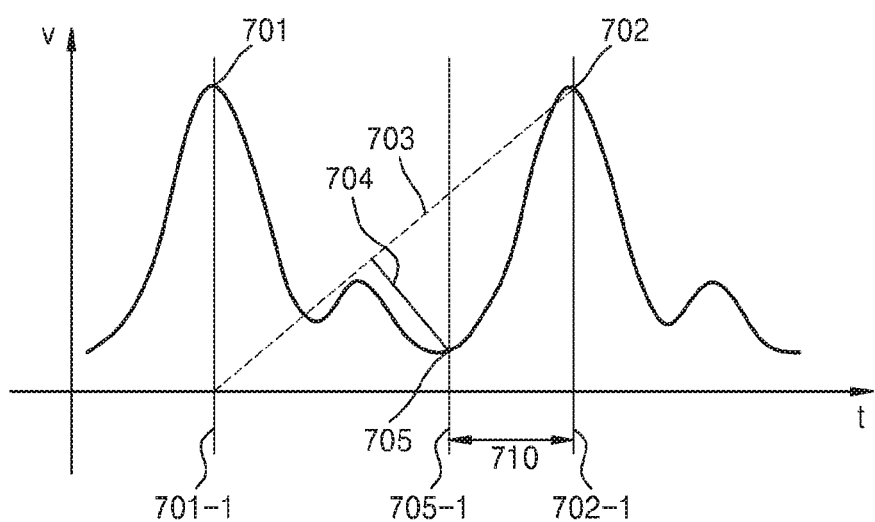
FIG. 7A is a diagram illustrating an acceleration time that is an example of a parameter.

FIG. 7A is a diagram illustrating an acceleration time that is an example of a parameter. The ultrasound imaging apparatus 300 may measure a value about at least one parameter that is used to estimate the fetal lung maturity based on the Doppler data. The Doppler data may be a Doppler wave having periods and representing a blood flow rate in the pulmonary trunk of the fetus. The at least one parameter may include the acceleration time and the ejection time. Here, the acceleration time is a time period from a reference time point to a point when the blood flow rate in the pulmonary trunk of the fetus is the highest according to contraction of heart. In addition, the ejection time is a time period from the reference time point to a point when the blood flow rate in the pulmonary trunk of the fetus is changed according to the relaxation of the heart.

Referring to the Doppler waveform shown in FIG. 7A, the ultrasound imaging apparatus 300 may detect a point 701 where the blood flow rate in the pulmonary trunk of the fetus peaks within a first period of the Doppler waveform. In addition, the ultrasound imaging apparatus 300 may detect a point 702 where the blood flow rate in the pulmonary trunk of the fetus peaks in a second period of the Doppler waveform. The ultrasound imaging apparatus 300 may detect a maximum distance 704 from a straight line 703 that connects a time point 701-1 of the point 701 where the blood flow rate peaks in the first period to the point 702 where the blood flow rate peaks in the second period, to the Doppler waveform. The ultrasound imaging apparatus 300 may determine a time point at a point 705 where the straight line of the maximum distance 704 and the Doppler waveform meet, as a reference time point 705-1. The ultrasound imaging apparatus 300 may determine a time period from the reference time point 705-1 to a time point 702-1 at the point 702 where the blood flow rate in the pulmonary trunk of the fetus peaks in the second period, as an acceleration time 710.

Here, one of ordinary skill in the art would appreciate that the acceleration time 710 may be determined by other methods than the above method.

Figure 7B:
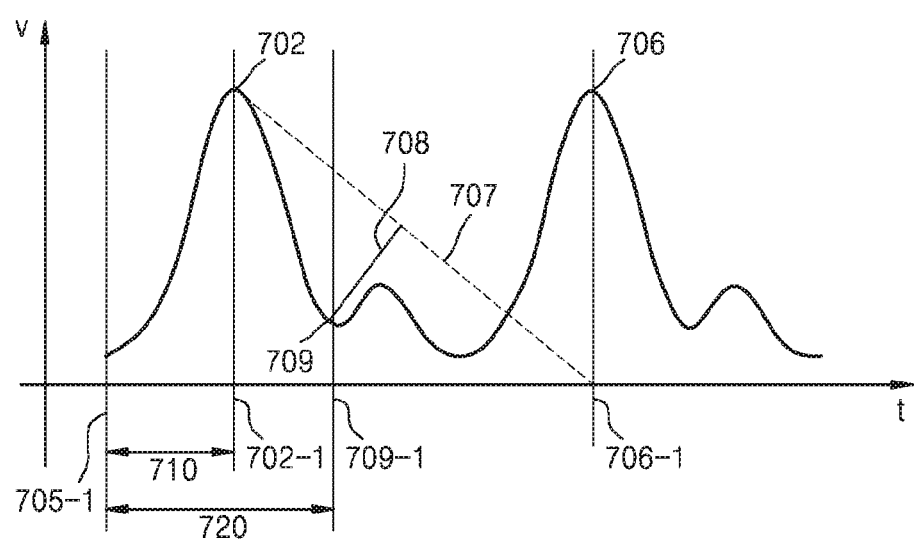
FIG. 7B is a diagram illustrating an ejection time that is another example of a parameter.

FIG. 7B is a diagram illustrating an ejection time that is another example of a parameter. The Doppler waveform of FIG. 7B is continuous from the Doppler waveform of FIG. 7A. Referring to the Doppler waveform of FIG. 7B, the ultrasound imaging apparatus 300 may detect a point 706 where the blood flow rate in the pulmonary trunk of the fetus peaks in a third period of the Doppler waveform. The ultrasound imaging apparatus 300 may detect a maximum distance 708 from a straight line 707, the straight light 707 connecting the point 702 where the blood flow rate in the pulmonary trunk of the fetus peaks in the second period to a time point 706-1 at a point 706 where the blood flow rate in the pulmonary trunk of the fetus peaks in the third period, to the Doppler waveform. The ultrasound imaging apparatus 300 may detect a time point 709-1 at a point 709 where the maximum distance 708 and the Doppler waveform meet. Then, the ultrasound imaging apparatus 300 may determine a time period from the reference time point 705-1 to the time point 709-1 at the point 709 on the Doppler waveform, as the ejection time 720.

Here, one of ordinary skill in the art would appreciate that the ejection time 720 may be determined by other methods than the above method.

FIG. 8 is a diagram illustrating data determining an estimated lung maturity of a fetus based on the acceleration time and the ejection time, according to an embodiment.

The ultrasound imaging apparatus 300 may estimate the fetal lung maturity by using the measured value about at least one parameter and a standard value of a plurality of fetuses about the at least one parameter according to the growth week number. As shown in a table 800 of FIG. 8, the ultrasound imaging apparatus 300 may determine the acceleration time and the ejection time based on the blood flow rate according to time in the pulmonary trunk, and may estimate the fetal lung maturity by using the acceleration time and the ejection time.

In detail, a transverse axis of the table 800 denotes a standard value of accelerations times obtained from a plurality of fetuses, and a longitudinal axis denotes a standard value of the ejection times obtained from the plurality of fetuses. Here, the standard value may be an average value of the values obtained from the plurality of fetuses according to the growth week number. Otherwise, the standard value may be a representative value calculated statistically from the values obtained from the plurality of fetuses according to the growth week number. The ultrasound imaging apparatus 300 compares the acceleration time and the ejection time with the standard values, and may estimate the estimated fetal lung maturity according to the comparison result.

As shown in the table 800, "24w2d±3d" denotes the estimated gestation of fetal lung maturity corresponding to 3 days before or after 24 weeks and 2 days. When the acceleration time is measured as 110 and the ejection time is measured as 220 from the Doppler data, the ultrasound imaging apparatus 300 may determine "24w5d±3d" as the estimated gestation of fetal lung maturity. One of ordinary skill in the art would appreciate that the fetal lung maturity may be estimated by using other ways than the above described method.

Figure 9A:
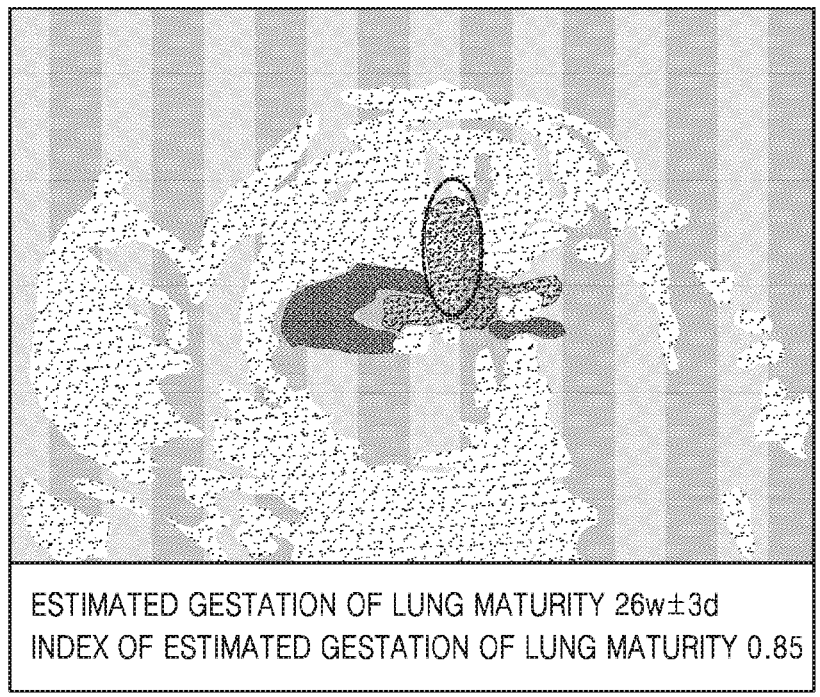
FIG. 9A is a diagram of a screen representing a result of lung maturity in an ultrasound imaging apparatus, according to an embodiment.

FIG. 9A is a diagram of a screen representing a result of lung maturity in the ultrasound imaging apparatus 300, according to an embodiment.

The ultrasound imaging apparatus 300 may display at least one of the estimated gestation of fetal lung maturity and an index representing the estimated fetal lung maturity gestations on a display screen 910 of the ultrasound imaging apparatus 300. The ultrasound imaging apparatus 300 may display the estimated gestation of fetal lung maturity and the index representing the estimated gestation of fetal lung maturity with the Doppler image of the fetus.

Like in a screen 910 illustrated in FIG. 9A, the ultrasound imaging apparatus 300 may represent the estimated gestation of fetal lung maturity as "26w±3d". In addition, the ultrasound imaging apparatus 300 may represent the index of the estimated gestation of fetal lung maturity as "0.85". The index of the estimated gestation of fetal lung maturity may be a ratio of the estimated gestation of lung maturity with respect to actual gestation of fetal lung maturity. In addition, the index of the estimated gestation of fetal lung maturity may be calculated according to an equation set in advance. The equation set in advance may be set by using a parameter related to the pulmonary blood flow index of the fetus. The parameter related to the pulmonary blood flow index may include a PSV, an EDV, a TAMV, and a TAPV, but is not limited thereto.

In addition, the index of the estimated gestation of fetal lung maturity may be generated by combining the above-mentioned parameters. In detail, the index of the estimated gestation of fetal lung maturity may be a ratio between the PSV and the EDV, as expressed by equations 3 and 4 illustrated with reference to FIG. 3.

In addition, the index of the estimated gestation of fetal lung maturity may be generated based on a difference between the PSV and the EDV. In detail, the index of the estimated gestation of fetal lung maturity may be calculated by the equation 5 and 6 described above with reference to FIGS. 5 and 6.

Figure 9B:
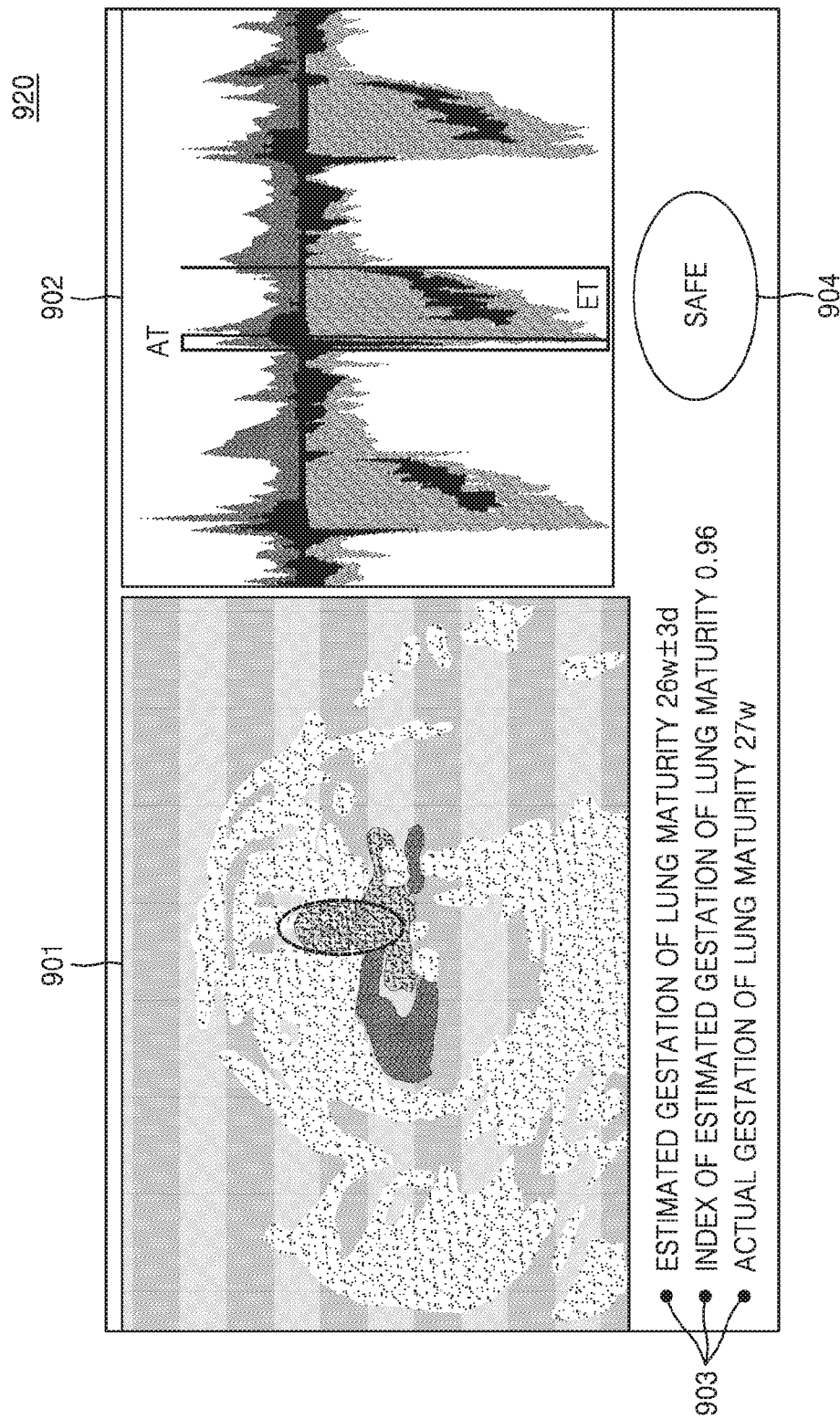
FIG. 9B is a diagram of a screen representing a result of lung maturity in an ultrasound imaging apparatus, according to another embodiment.

FIG. 9B is a diagram of a screen representing a result of lung maturity in the ultrasound imaging apparatus 300, according to another embodiment.

The ultrasound imaging apparatus 300 may display the estimated gestation of fetal lung maturity, the index representing the estimated gestation of fetal lung maturity, and the actual gestation of fetal lung maturity on a display screen 920 of the ultrasound imaging apparatus 300. In addition, the ultrasound imaging apparatus 300 may display a result 903 of the fetal lung maturity with a Doppler image 901 and a Doppler spectrum 902 of the fetus.

In detail, the fetal lung maturity result 902 may include the estimated gestation of fetal lung maturity, the index representing the estimated gestation of fetal lung maturity, and the actual gestation of fetal lung maturity, but is not limited thereto.

In addition, the ultrasound imaging apparatus 300 may determine safety of the fetal lung maturity, based on at least one of the estimated gestation of fetal lung maturity according to gestational age, and the index representing the estimated gestation of fetal lung maturity. The ultrasound imaging apparatus 300 may display a result of evaluating the safety of the fetal lung maturity on the screen.

In detail, as shown in FIG. 9B, the estimated gestation of fetal lung maturity denotes "26w±3d" and the actual gestation of fetal lung maturity is 27 weeks. Regarding the lung maturity, it may be set to determine the lung maturity being safe when the estimated gestation of the lung maturity and the actual gestation of lung maturity differ from each other by two weeks or less. Therefore, since the difference between the estimated gestation of lung maturity and the actual gestation of lung maturity is two weeks or less, the ultrasound imaging apparatus 300 may determine the fetal lung maturity being safe, and may display a "safe" index 904 on the screen 920.

In addition, regarding the lung maturity, it may be set to determine the lung maturity being safe when the index of the estimated gestation of lung maturity has a value of 10% or less with respect to a reference value 1. Therefore, as shown in FIG. 9B, since the index of the estimated gestation of lung maturity is 0.96, the lung maturity may be determined being safe. The ultrasound imaging apparatus 300 may display the "safe" index 904 on the screen 920 as a result of evaluating safety of the lung maturity.

In addition, processes of determining whether the lung maturity is safe or not may be set by using other parameters than the above described parameter.

Figure 9C:
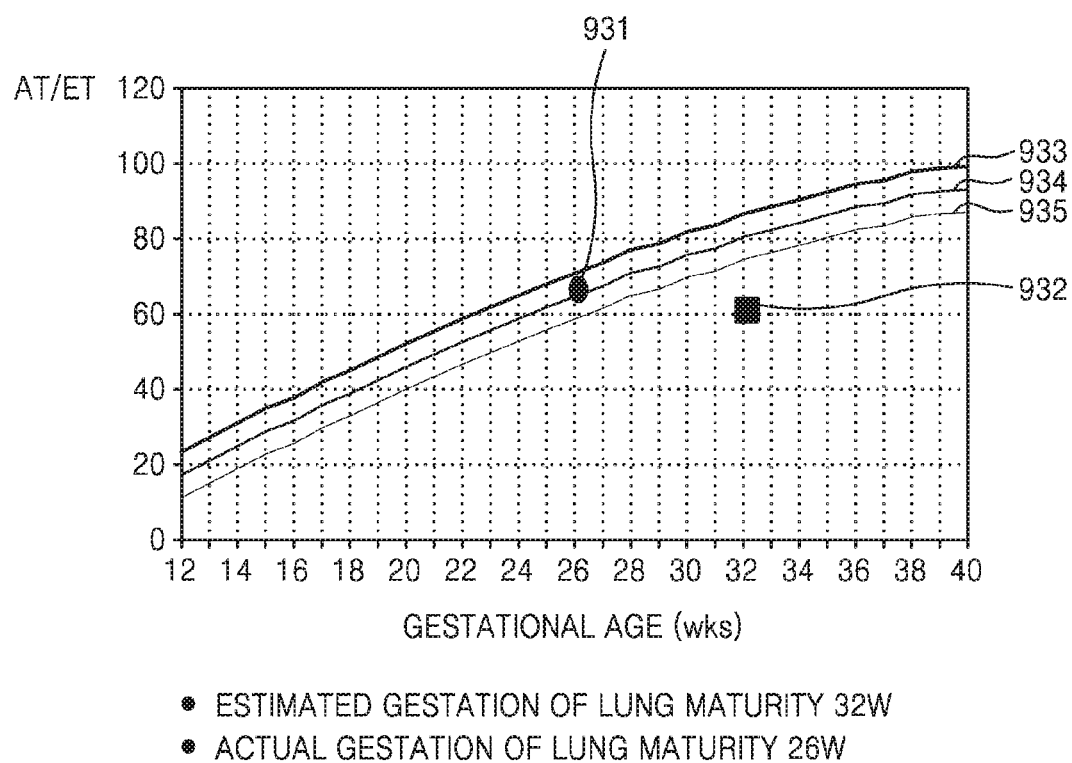
FIG. 9C is a diagram of a screen representing a result of lung maturity in an ultrasound imaging apparatus, according to another embodiment.

FIG. 9C is a diagram of a screen representing a result of lung maturity in the ultrasound imaging apparatus 300, according to another embodiment.

The ultrasound imaging apparatus 300 may display the result of estimated lung maturity on a screen 930 of the display as a graph. The ultrasound imaging apparatus 300 may represent the estimated gestation of the fetal lung maturity and the actual gestation of the fetus to be distinguished from each other on the graph.

In detail, as shown in FIG. 9C, a transverse axis denotes gestation of the fetal lung maturity and a longitudinal axis denotes a ratio of the acceleration time with respect to the ejection time. One of ordinary skill in the art would appreciate that the longitudinal axis may be set as an index related to the fetal lung maturity rather than the ratio of the acceleration time with respect to the ejection time.

The ultrasound imaging apparatus 300 may display the indexes related to the lung maturity of a plurality of fetuses on the graph (933, 934, and 935). The ultrasound imaging apparatus 300 may represent a standard value according to the gestation of lung maturity as a solid line 934 on the graph. Here, the standard value is a representative value of the index related to the lung maturity of a plurality of fetuses. In addition, the ultrasound imaging apparatus 300 may represent a range, in which the lung of the fetus may be determined safe based on the standard value, as a solid line 933 and a solid line 935 on the graph.

In addition, the ultrasound imaging apparatus 300 may represent a current status of the fetus according to the "estimated gestation of lung maturity" and "a ratio of the acceleration time with respect to the ejection time" as a coordinate 932 on the graph. The ultrasound imaging apparatus 300 may represent a normal status of the fetus according to the actual gestation of the fetal lung maturity as a coordinate 931 on the graph. The ultrasound imaging apparatus 300 may represent the coordinate 931 and the coordinate 932 in different shapes or different colors to be distinguished from each other.

When the coordinate 932 representing the current status of the fetus does not exist between the solid line 933 and the solid line 935 based on the standard value 934, the ultrasound imaging apparatus 300 may determine the fetal lung maturity unsafe and may display information representing the unsafe condition on the screen. In addition, the ultrasound imaging apparatus 300 may output the safety of the fetal lung maturity as a voice.

In addition, the ultrasound imaging apparatus 300 may display information representing the estimated gestation of the fetal lung maturity and the actual gestation of lung maturity on the display screen 930.

Figure 10:
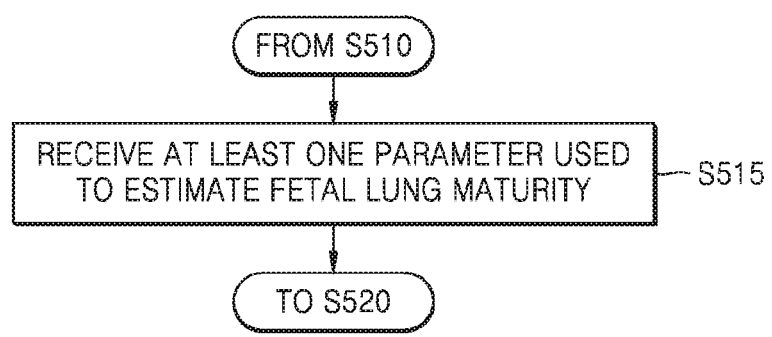
FIG. 10 is a flowchart illustrating a method of operating an ultrasound imaging apparatus, according to another embodiment.

FIG. 10 is a flowchart illustrating a method of operating the ultrasound imaging apparatus 400, according to another embodiment.

In operation S515 of FIG. 10, the ultrasound imaging apparatus 400 may receive at least one parameter used to estimate fetal lung maturity. Here, the at least one parameter may be a parameter related to an index of pulmonary blood flow of the fetus. In detail, the parameter may include an acceleration time and an ejection time. Descriptions about the acceleration time and the ejection time are omitted.

The ultrasound imaging apparatus 400 may estimate the fetal lung maturity based on the received at least one parameter. If a user inputs "acceleration time" and "ejection time" via the user interface of the ultrasound imaging apparatus 400 in order to estimate the fetal lung maturity, the ultrasound imaging apparatus 400 may determine the "acceleration time" and the "ejection time" from the Doppler data and may determine the fetal lung maturity by using a value of the acceleration time and a value of the ejection time.

In addition, if the user inputs a first parameter for estimating the fetal lung maturity, the ultrasound imaging apparatus 400 may output information of a second parameter that is related to the first parameter and may be used together with the first parameter in estimating the fetal lung maturity. Here, the information about the second parameter may be displayed on the screen or may be output as voice. In addition, the ultrasound imaging apparatus 400 may display an equation for estimating the fetal lung maturity by using the first parameter on the screen.

As shown in FIG. 10, the ultrasound imaging apparatus 400 may execute operation S510 illustrated in FIG. 5, operation S515 illustrated in FIG. 10, and operation S520 illustrated in FIG. 5. In addition, the ultrasound imaging apparatus 400 may execute operation S515 in other orders than the order illustrated in FIG. 10. In detail, after executing operation S530 of FIG. 5, the ultrasound imaging apparatus 400 additionally execute operation S515, and may estimate the fetal lung maturity based on the input parameter.

Figure 11:
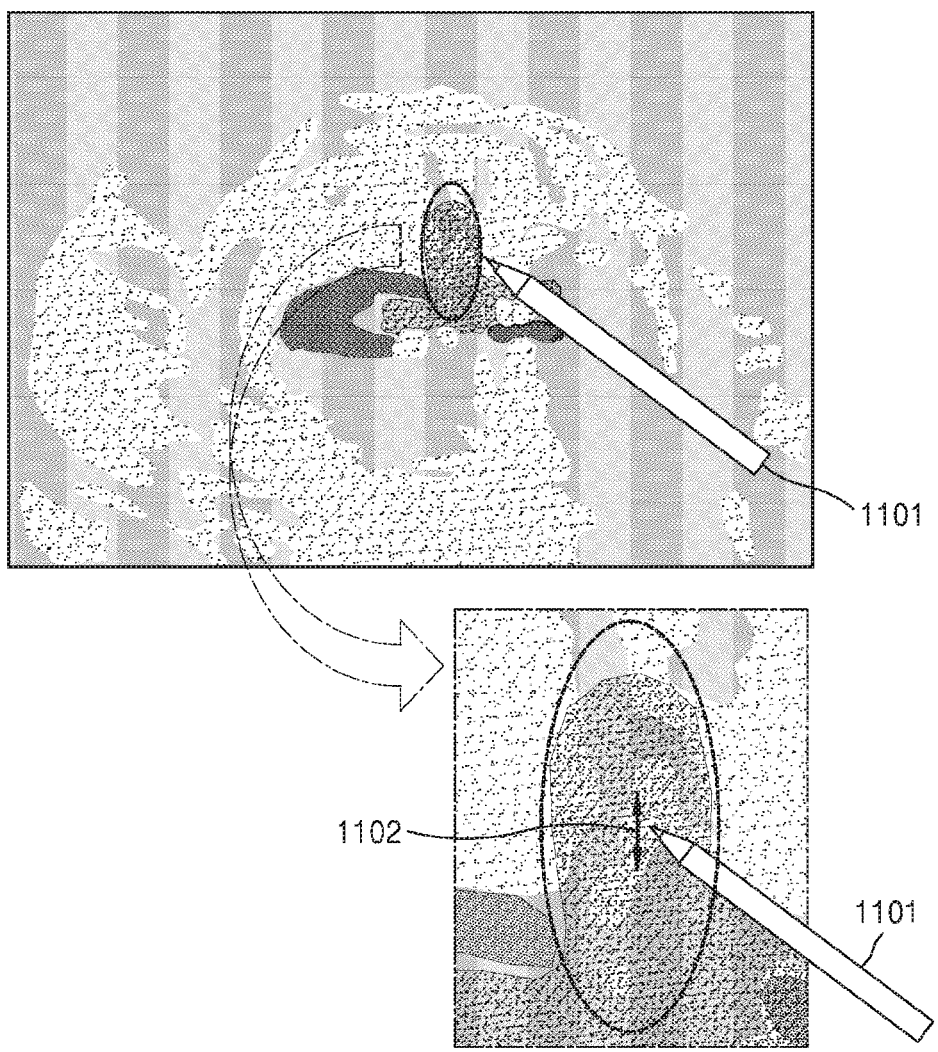
FIG. 11 is a diagram illustrating processes of estimating lung maturity of a fetus based on user input, according to an embodiment.

FIG. 11 is a diagram illustrating processes of estimating lung maturity of a fetus based on user input, according to an embodiment.

The ultrasound imaging apparatus 400 may receive an input for setting a boundary of a fetal lung area from a Doppler image 1100 obtained from ultrasound data. The ultrasound imaging apparatus 400 may determine a size of the fetal lung based on the boundary. The ultrasound imaging apparatus 400 may compare the size of the fetal lung with a standard value of a plurality of fetuses, and may determine fetal lung maturity according to a comparison result. Here, the standard value is a representative value of lung sizes of a plurality of fetuses, according to the gestation. The standard value may be an average value of the lung sizes of a plurality of fetuses according to the gestation, or a value calculated statistically. One of ordinary skill in the art would appreciate that the standard value may be set in other ways than the above described method.

In addition, the ultrasound imaging apparatus 400 may determine an estimated gestation of fetal lung maturity based on the size of the fetal lung, and may estimate the fetal lung maturity after comparing the estimated gestation with actual gestation of the fetal lung maturity. In addition, if the size of the fetal lung may exceed a safe range based on the standard value, the ultrasound imaging apparatus 400 may display information notifying that the fetal lung is unsafe.

The user may input boundary setting of the fetal lung area on the Doppler image of the fetus via a control panel, a trackball, a mouse, a keyboard, etc., of the ultrasound imaging apparatus 400.

The ultrasound imaging apparatus 400 may receive the input of boundary setting from a touch input of the user via various input devices. In detail, the ultrasound imaging apparatus 400 may receive the input of boundary setting of the fetal lung area from a hand of the user, a physical tool, a stylus pen 1101, etc.

As shown in FIG. 11, the user may indicate a portion 1102 corresponding to a width of the fetal lung area as a segment on the Doppler image 1100 by using a stylus pen 1101. The ultrasound imaging apparatus 400 may calculate a size of the fetal lung based on a width input by the user. The ultrasound imaging apparatus 400 may compare the size of the fetal lung and a standard value of the sizes of lungs of a plurality of fetuses, and determine the estimated gestation of the fetal lung maturity. The ultrasound imaging apparatus 400 may estimate the fetal lung maturity based on the estimated gestation of the fetal lung maturity and the actual gestation of the fetal lung maturity.

Figure 12:
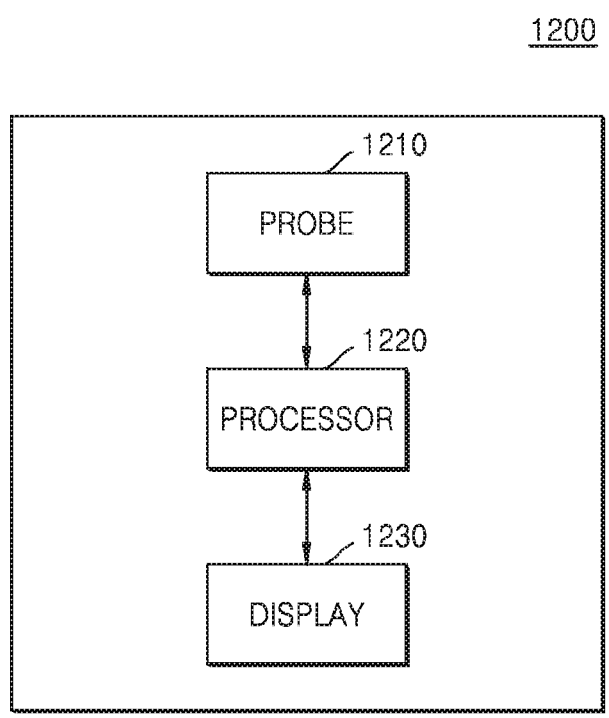
FIG. 12 is a block diagram of an ultrasound imaging apparatus according to an embodiment.

FIG. 12 is a block diagram of an ultrasound imaging apparatus 1200 according to an embodiment.

The ultrasound imaging apparatus 1200 may include a probe 1210, a processor 1220, and a display 1230. However, not all the elements in FIG. 12 are essential elements. The ultrasound imaging apparatus 1200 may include more or less elements than the elements shown in FIG. 12. Hereinafter, the elements will be described below.

Detailed descriptions about the probe 1210 described above with reference to FIG. 3 are omitted. The probe 1210 receives ultrasound data from an object.

The processor 1220 may obtain a Doppler image of the object based on the ultrasound data. The Doppler image may be at least one of a color Doppler image, a power Doppler image, a tissue Doppler image, a vector Doppler image, and a spectral Doppler image, but is not limited thereto.

The processor 1220 sets a region of interest in the object within the Doppler image, and may obtain the Doppler data corresponding to motion having periodicity of the object from the region of interest for a plurality of first sample periods. Here, the object may be the heart, but is not limited thereto.

The processor 1220 may obtain an actual period of the motion of the object based on a frequency analysis of the Doppler data. Here, the processor 1220 may obtain the actual period of the motion of the object by applying a Fast Fourier Transform to the Doppler data. The processor 1220 may rearrange the Doppler data based on the actual period. In detail, the processor 1220 may arrange the Doppler data corresponding to an actual first period of the object. The processor 1220 may arrange Doppler data corresponding to an actual second period of the object to overlap with the Doppler data corresponding to the actual first period. The processor 1220 may arrange Doppler data corresponding to an actual third period of the object to overlap with the Doppler data corresponding to the actual first period.

The processor 1220 may obtain Doppler data corresponding to the motion having periodicity of the object for a plurality of second sample periods. The processor 1220 may rearrange the Doppler data obtained for the plurality of first sample periods and the Doppler data obtained for the plurality of second sample periods, based on actual periods.

If the actual period of the motion of the object is in a multiple relation with the first sample period, the processor 1220 may set the second sample period that is not in multiple relation with the actual period. The processor 1220 may obtain the Doppler data corresponding to the motion of the object from the region of interest for the plurality of second sample periods. The processor 1220 may rearrange the Doppler data that is obtained for the plurality of second sample periods based on the actual period.

In addition, the processor 1220 may obtain the Doppler data by delaying a predetermined time period between the plurality of periods.

The display 1230 displays a predetermined screen. In detail, the display 1230 displays a predetermined screen according to control of the processor 1220. The display 1230 includes a display panel, and may display a medical image, etc. on the display panel.

The display 1230 may display the Doppler image. Modes for providing the Doppler image may include a Brightness mode (B-mode) for providing B-mode images, a color Doppler mode (C-mode) or a power Doppler mode (P-mode) for providing color flow images, and a Doppler mode (D-mode) for providing a Doppler spectrum, and the ultrasound imaging apparatus 1200 may display the Doppler image on the screen of the display 120 according to one of the plurality of modes.

In addition, the display 1230 may display rearranged Doppler data.

The ultrasound imaging apparatus 1200 includes a central processor that controls all operations of the probe 1210, the processor 1220, and the display 1230. The central processor may be implemented as an array of a plurality of logic gates, or as a combination of a universal microprocessor and a memory storing programs that may be executed in the microprocessor. In addition, one of ordinary skill in the art would appreciate that the central processor may be implemented by other types of hardware.

Figure 13:
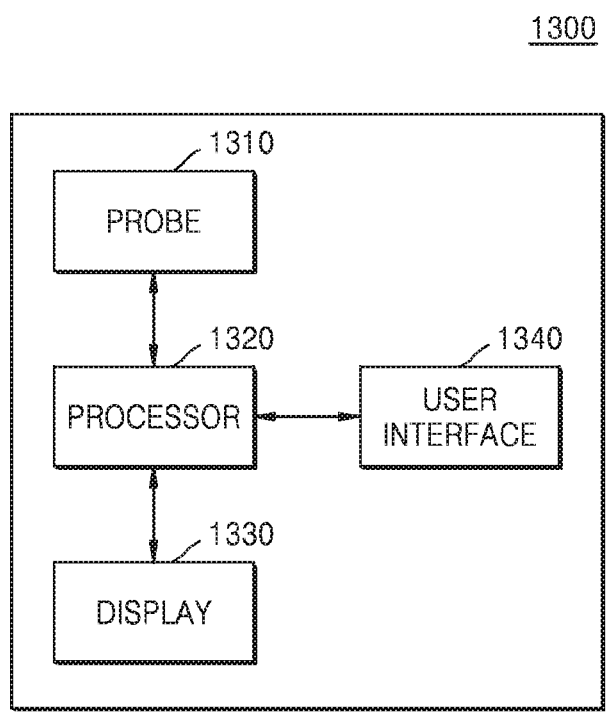
FIG. 13 is a block diagram of an ultrasound imaging apparatus according to another embodiment.

FIG. 13 is a block diagram of an ultrasound imaging apparatus 1300 according to another embodiment.

The ultrasound imaging apparatus 1300 may include a probe 1310, a processor 1320, a display 1330, and a user interface 1340.

In FIG. 13, the probe 1310, the processor 1320, and the display 1330 of the ultrasound imaging apparatus 1300 respectively correspond to the probe 1210, the processor 1220, and the display 1230 of the ultrasound imaging apparatus 1200 illustrated with reference to FIG. 12, and thus, detailed descriptions thereof are omitted. The ultrasound imaging apparatus 1300 may include more or less elements than the elements shown in FIG. 13. Hereinafter, the elements will be described below.

The user interface 1340 is an apparatus for receiving data for controlling the ultrasound imaging apparatus 1300 from a user. The processor 1320 may control the display 1330 to generate and output a user interface 1340 screen for receiving a predetermined command or data from the user. The display 1330 may display a screen for receiving an input of setting a region of interest in the object, on the display panel.

The user interface 1340 may receive a user input for setting the region of interest in the object, within the Doppler image. The processor 1320 may obtain Doppler data corresponding to motion having periodicity of the object based on the user input.

Here, the user interface 1340 may include hardware such as a keypad, a mouse, a touch panel, a touch screen, a track ball, a jog switch, etc., but is not limited thereto. In addition, the user interface 1340 may further include various input units such as a voice recognition sensor, a gesture recognition sensor, a fingerprint sensor, an iris sensor, a depth sensor, a distance sensor, etc.

In addition, the ultrasound imaging apparatus 1300 may further include a storage (not shown) and a communicator (not shown). The storage (not shown) may correspond to the memory 180 of FIG. 1, and the communicator (not shown) may correspond to the communicator 170 of FIG. 1. The storage (not shown) may store data regarding the ultrasound images (e.g., ultrasound images, ultrasound data, scanning data, diagnosis data of a patient, etc.) and data transmitted to the ultrasound imaging apparatus 1300 from an external device. The data transmitted from the external device may include information about a patient, data necessary for diagnosing and treating the patient, previous history of the patient, medical work list corresponding to prescription for the patient, etc.

The storage (not shown) may store rearranged Doppler data. In detail, the storage may store "a result of arranging Doppler data corresponding to the actual first period of the object," "a result of arranging Doppler data corresponding to the actual second period of the object to overlap with Doppler data corresponding to the actual first period," and "a result of arranging Doppler data corresponding to the actual third period of the object to overlap with Doppler data corresponding to the actual first period".

In addition, the storage (not shown) may respectively store the Doppler data obtained for the plurality of first sample periods and the Doppler data obtained for the plurality of second sample periods, from the Doppler image.

The communicator (not shown) may receive the Doppler image of the object and the Doppler data of the object from an external device, and/or may transmit the Doppler image of the object, the Doppler data of the object, and rearranged Doppler data to the external device. For example, the communicator (not shown) may be connected to a wireless probe or an external device via a communication network according to Wi-Fi or Wi-Fi direct.

In detail, a wireless communication network the communicator may access may include wireless LAN, Wi-Fi, Bluetooth, ZigBee, Wi-Fi direct (WFD), ultra wideband (UWB), infrared data association (IrDA), Bluetooth low energy (BLE), and near field communication (NFC), but is not limited thereto.

The ultrasound imaging apparatus 1300 includes the central processor for controlling all operations of the probe 1310, the processor 1320, the display 1330, the user interface 1340, the storage (not shown), and the communicator (not shown). The central processor may be implemented as an array of a plurality of logic gates, or as a combination of a universal microprocessor and a memory storing programs that may be executed in the microprocessor. In addition, one of ordinary skill in the art would appreciate that the central processor may be implemented by other types of hardware.

Hereinafter, various operations or applications that the ultrasound imaging apparatus 1200 or 1300 performs will be described. Even when the probe 1210 or 1310, the processor 1220 or 1320, the display 1230 or 1330, the user interface 1340, the storage (not shown), and the communicator (not shown) are not specifically described, features that would have been understood or expected by one of ordinary skill in the art may be regarded as their general features. The scope of the present disclosure is not limited to a name or physical/logical structure of a specific component.

Figure 14:
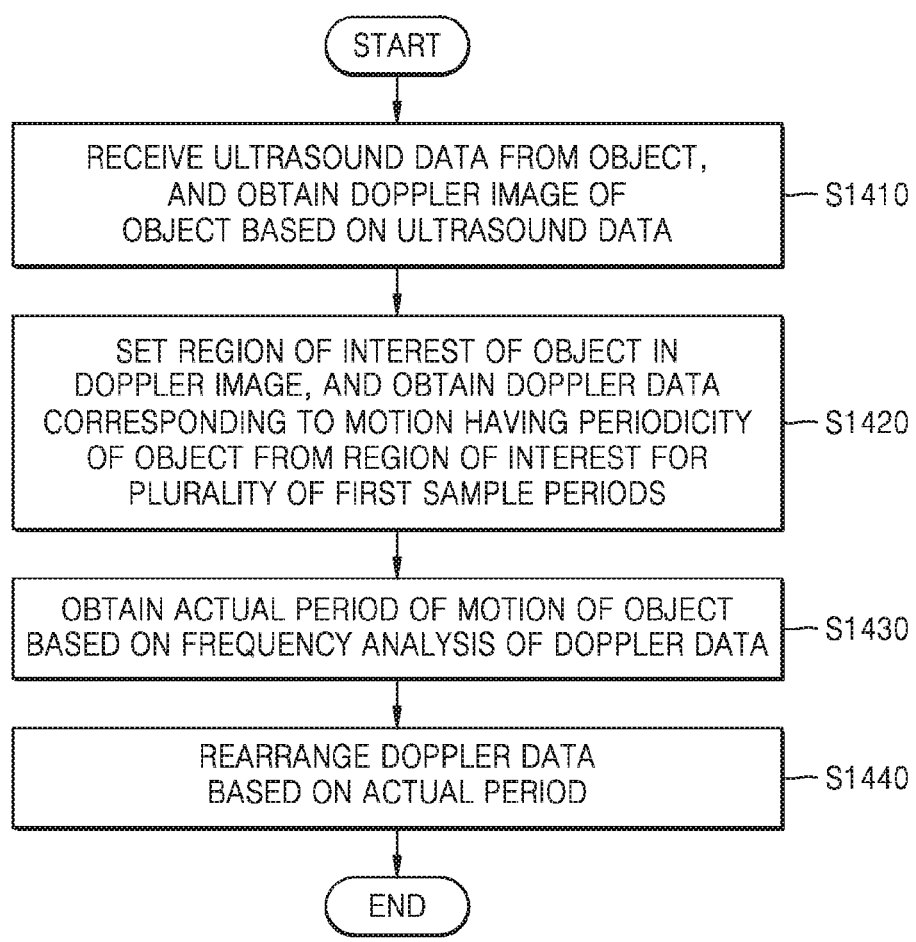
FIG. 14 is a flowchart illustrating a method of operating an ultrasound imaging apparatus, according to an embodiment.

FIG. 14 is a flowchart illustrating a method of operating the ultrasound imaging apparatus 1200, according to an embodiment.

Hereinafter, operations of the ultrasound imaging apparatus 1200 may be applied to the ultrasound imaging apparatus 1300.

In operation S1410 of FIG. 14, the ultrasound imaging apparatus 1200 may receive ultrasound data from the object, and may obtain a Doppler image of the object based on the ultrasound data. Here, the object may be the heart, but is not limited thereto. In addition, the Doppler image may be at least one of a color Doppler image, a power Doppler image, a tissue Doppler image, a vector Doppler image, and a spectral Doppler image, but is not limited thereto.

In operation S1420, the ultrasound imaging apparatus 1200 sets a region of interest of the object in the Doppler image, and may obtain Doppler data corresponding to motion having periodicity of the object from the region of interest. The ultrasound imaging apparatus 1200 may obtain the Doppler data for a plurality of first sample periods. In addition, the ultrasound imaging apparatus 1200 may obtain Doppler data for a plurality of second sample periods from the region of interest, wherein the second sample period is different from the first sample period.

In addition, the ultrasound imaging apparatus 1200 may obtain the Doppler data by delaying a predetermined time period among the plurality of periods, while obtaining the Doppler data for the plurality of first sample periods. In detail, the ultrasound imaging apparatus 1200 obtains the Doppler data of a first period by the first sample period, and after a first delay time has passed, and obtains the Doppler data of a second period by the first sample period. After that, the ultrasound imaging apparatus 1200 may obtain the Doppler data of a third period by the first sample period, after the first delay time has passed. The ultrasound imaging apparatus 1200 may obtain the Doppler data for the plurality of periods in the above-described way.

In operation S1530, the ultrasound imaging apparatus 1200 may obtain the actual period of the motion of object, based on a frequency analysis of the Doppler data. The ultrasound imaging apparatus 1200 may obtain the actual period of the object's motion by applying a Fast Fourier Transform to the Doppler data. The ultrasound imaging apparatus 1200 may obtain the actual period of the object's motion in other ways than the above Fast Fourier Transform. In addition, the ultrasound imaging apparatus 1200 may receive the actual period of the object's motion from an external device. Here, the external device may be an apparatus for obtaining, storing, processing, or using data related to the ultrasound image, and may be a medical imaging apparatus, a medical server, a portable terminal, or all kinds of computing devices capable of using and processing medical images. For example, the external device may be a medical diagnosis apparatus provided in a medical institute such as a hospital. In addition, the external device may include a server for recording and storing previous medical history of the patient in the hospital, a medical imaging apparatus for a doctor to read the medical images, etc.

In addition, when the actual period of the object's motion is in multiple relation with the first sample period, the ultrasound imaging apparatus 1200 sets the second sample period that is not in the multiple relation with the actual period, and may obtain the Doppler data for the plurality of second sample periods from the region of interest in the object.

In operation S1540, the ultrasound imaging apparatus 1200 may rearrange the Doppler data based on the actual period. The ultrasound imaging apparatus 1200 may display the rearranged Doppler data on the display screen.

Regarding the rearrangement of the Doppler data, the ultrasound imaging apparatus 1200 may arrange the Doppler data corresponding to the actual first period of the object. The ultrasound imaging apparatus 1200 may arrange the Doppler data corresponding to an actual second period of the object to overlap with the Doppler data corresponding to the actual first period. The ultrasound imaging apparatus 1200 may arrange the Doppler data corresponding to an actual third period of the object to overlap with the Doppler data corresponding to the actual first period.

In addition, the ultrasound imaging apparatus 1200 may rearrange the Doppler data that is obtained for the plurality of first sample periods and the Doppler data that is obtained for the plurality of second sample periods, based on the actual period. In detail, the ultrasound imaging apparatus 1200 may obtain first Doppler data by arranging the Doppler data obtained in the first sample period of the object and the Doppler data obtained in the second sample period of the object, according to the actual first period.

The ultrasound imaging apparatus 1200 may obtain second Doppler data by arranging the Doppler data obtained in the first sample period and the Doppler data obtained in the second sample period after the actual first period until the actual second period in a temporal manner, to overlap with the first Doppler data. Likewise, the ultrasound imaging apparatus 1200 may obtain third Doppler data by arranging the Doppler data obtained in the first sample period and the Doppler data obtained in the second sample period after the actual second period until the actual third period in a temporal manner, to overlap with the first Doppler data. Finally, the ultrasound imaging apparatus 1200 may display the third Doppler data.

Figure 15:
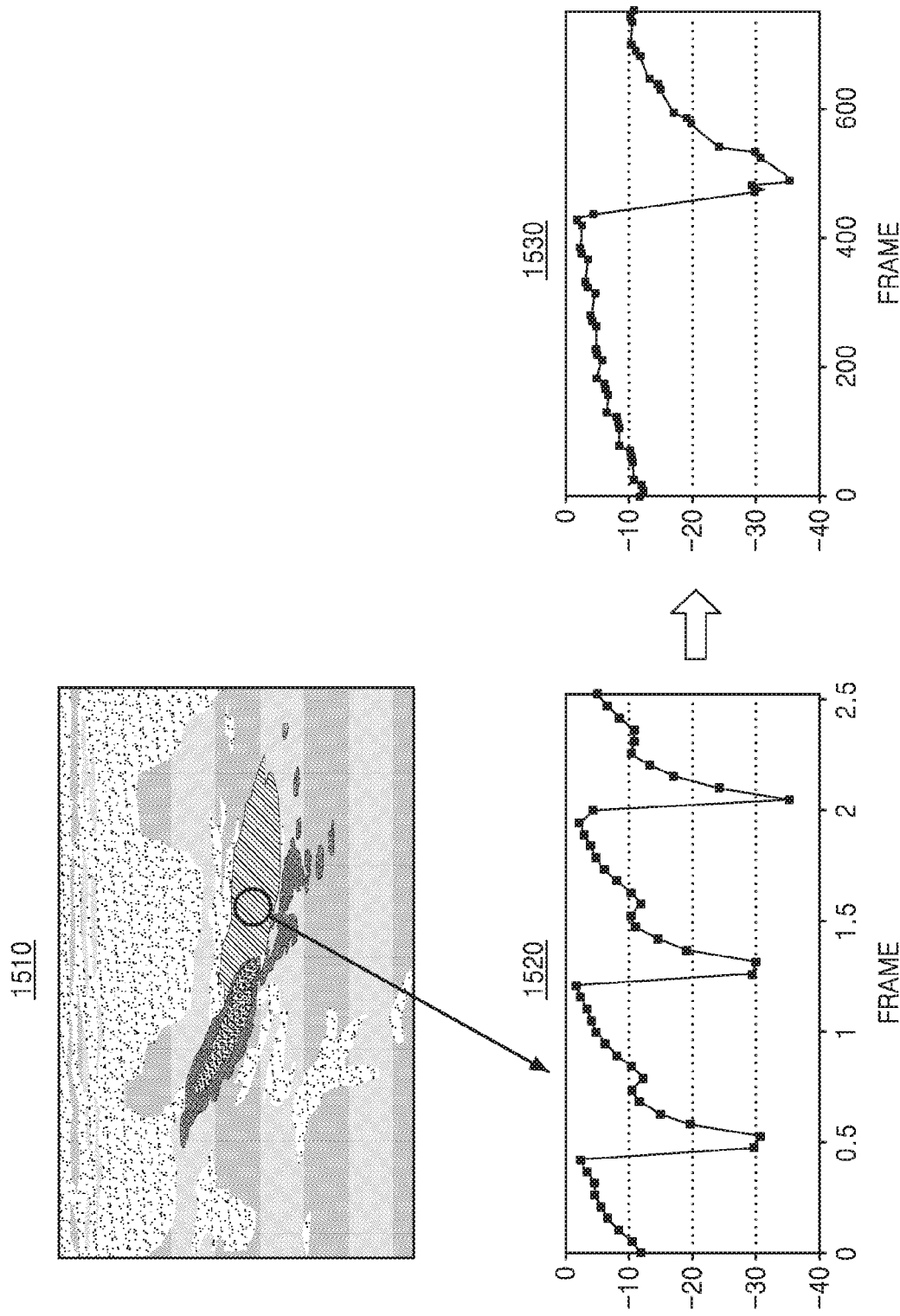
FIG. 15 is a diagram illustrating processes of ensuring temporal resolution of Doppler data that is necessary for diagnosing an object by using a Doppler image, according to an embodiment.

FIG. 15 is a diagram illustrating processes of ensuring temporal resolution of Doppler data that is necessary for diagnosing an object by using a Doppler image, according to an embodiment.

The ultrasound imaging apparatus 1200 generates an ultrasound image by using ultrasound data. The ultrasound imaging apparatus 1200 may provide the ultrasound image according to at least one of the B-mode for providing the B-mode image, the C-mode or the P-mode for providing a color flow image, and the D-mode for providing the Doppler spectrum.

As shown in an image 1510 of FIG. 15, the ultrasound imaging apparatus 1300 may display the ultrasound image in the C-mode for providing the color flow image. Here, the color flow image may include a color Doppler image and a power Doppler image. In addition, the ultrasound imaging apparatus 1300 may display the color Doppler image, and may receive a user input for setting a region of interest in the color Doppler image. Here, the ultrasound imaging apparatus 1300 may receive the user input via a touch input. The ultrasound imaging apparatus 1300 may include a touch sensor or a proximity sensor for sensing the touch input. For example, the touch sensor may be a type of a touch film, a touch sheet, a touch pad, etc. The ultrasound imaging apparatus 1300 may receive a signal for setting the region of interest according to the touch input of the user via various input tools. In detail, the ultrasound imaging apparatus 1300 may receive the signal for setting the region of interest in the object via a hand of the user, a physical tool, a stylus pen, etc.

Referring to an image 1520 of FIG. 15, the ultrasound imaging apparatus 1200 or 1300 may obtain the Doppler data corresponding to the motion having periodicity of the object from the region of interest on the color Doppler image. The ultrasound imaging apparatus 1200 or 1300 may obtain the Doppler data of the plurality of first sample periods at the same location on the color Doppler image. As shown in the image 1520, the Doppler data obtained from the color Doppler image has frequent occurrence of discontinued points, and may have a low temporal resolution. In order to diagnose the object precisely, the ultrasound imaging apparatus 1200 or 1300 needs to provide accurate Doppler data by improving the temporal resolution of the Doppler data.

Referring to an image 1530 of FIG. 15, the ultrasound imaging apparatus 1200 or 1300 may obtain an actual period of the object's motion based on the Doppler data. The ultrasound imaging apparatus 1200 or 1300 may rearrange the Doppler data obtained for the plurality of first sample periods, based on the actual period. The method of rearranging the Doppler data will be described with reference to FIGS. 16A, 16B, 17A, and 17B. The ultrasound imaging apparatus 1200 or 1300 may display the rearranged data on the display screen. As shown in the image 1530, the rearranged Doppler data has a lower frequency of the discontinued points and higher temporal resolution than those of the Doppler data of the image 1520.

Figure 16A:
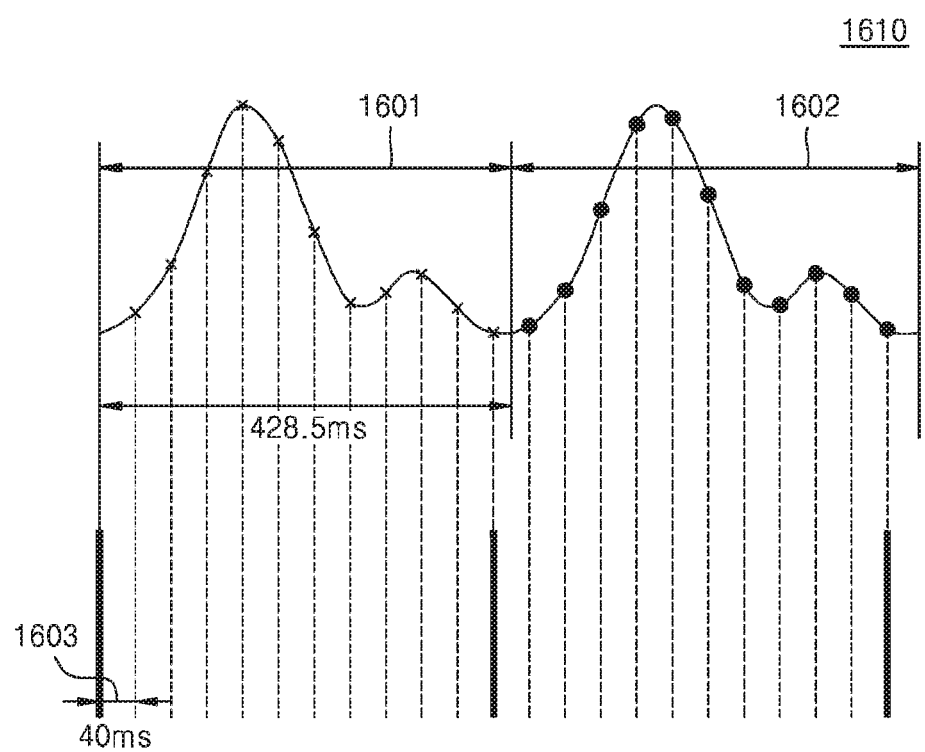
FIG. 16A is a diagram illustrating processes of obtaining Doppler data according to a first sample period, according to an embodiment.

FIG. 16A is a diagram illustrating processes of obtaining Doppler data according to a first sample period, according to an embodiment.

The ultrasound imaging apparatus 1200 transmits ultrasound waves to the heart of a fetus, and obtains a Doppler image from a reflected signal. The ultrasound imaging apparatus 1200 may obtain Doppler data related to heartbeat of the fetus from the Doppler image.

It is assumed that the heartbeat of the fetus is 140 BPM. That is, one period of the heartbeat of the fetus is 428.5 ms. The ultrasound imaging apparatus 1200 may obtain Doppler data for a plurality of first sample periods 1603 during an actual first period 1601 and an actual second period 1602 of the heartbeat of the fetus. As shown in a graph 1610 of FIG. 16A, the Doppler data obtained according to the first sample period 1603 during the actual first period 1601 is represented as X, and the Doppler data obtained according to the first sample period 1603 during the actual second period 1602 is represented as O.

Figure 16B:
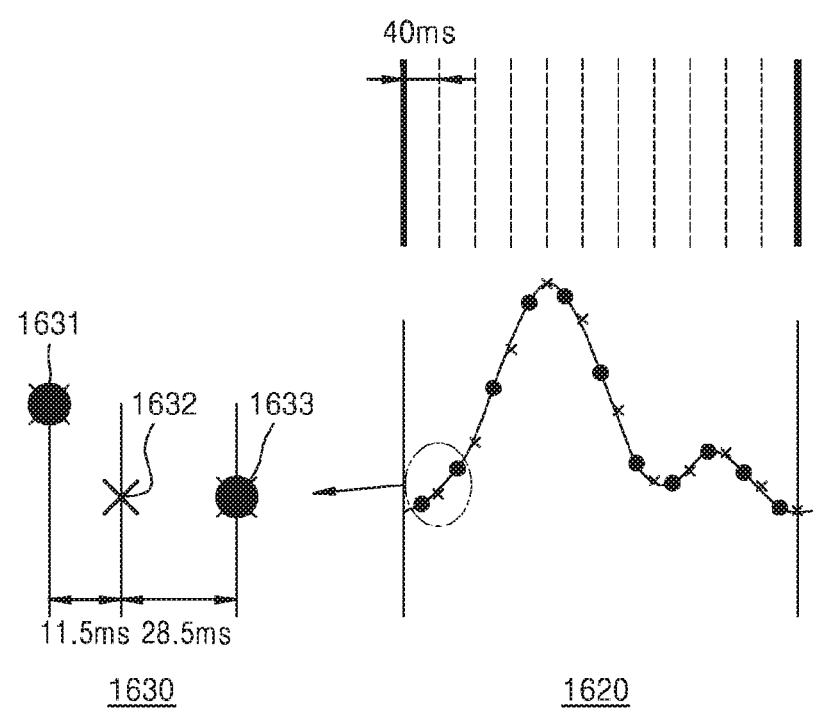
FIG. 16B is a diagram illustrating rearranging of obtained Doppler data, according to an embodiment.

FIG. 16B is a diagram illustrating rearranging of obtained Doppler data, according to an embodiment.

Referring to a graph 1620 of FIG. The ultrasound imaging apparatus 1200 may obtain second Doppler data by overlapping the Doppler data sampled in the first sample period 1603 during the actual second period 1602 of the heartbeat of the fetus with the first Doppler data.

Referring to an image 1630 of FIG. 16B, the Doppler data obtained by overlapping the Doppler data sampled in the first sample period 1603 during the actual first period 1601 of the heartbeat of the fetus with the Doppler data sampled in the first sample period 1603 during the actual second period 1602 of the heartbeat of the fetus may include more information about the heartbeat of the fetus than that of the Doppler data sampled in the first sample period 1603 during the actual first period 1601.

As shown in the image 1630 of FIG. 16B, the Doppler data obtained by the ultrasound imaging apparatus 1200 according to the first sample period 1603 before 80 ms from rearranging the Doppler data is only the Doppler data 1632 sampled at 40 ms. However, as a result of rearranging the Doppler data, which is sampled according to the first sample period 1603 during the actual second period of the heartbeat of the fetus, according to the actual first period 1601, the Doppler data obtained by the ultrasound imaging apparatus 1200 before 80 ms may increase to three pieces 1631, 1632, and 1633. Therefore, the ultrasound imaging apparatus 1200 may obtain more pieces of information about the heartbeat of the fetus during the same time, thereby improving a temporal accuracy.

Although the method of rearranging the Doppler data according to the first sample period during the actual first and second periods of the heartbeat of the fetus is described with reference to FIGS. 16A and 16B, Doppler data of the heartbeat of the fetus may be provided more accurately by the ultrasound imaging apparatus 1200, provided that the Doppler data is obtained during actual three or more periods and rearranged.

In addition, when the period of the heartbeat of the fetus is 400 ms and the first sample period is 40 ms, the actual period of the heartbeat of the fetus and the first sample period are in a multiple relation with each other. In this case, when the Doppler data obtained according to the first sample period during the actual first and second periods is rearranged according to the actual first period, the Doppler data obtained according to the first sample period during the actual second period becomes equal to the Doppler data obtained according to the first sample period during the actual first period. Therefore, the ultrasound imaging apparatus 1200 may set the second sample period that is not in the multiple relation with the actual period. The ultrasound imaging apparatus 1200 obtains the Doppler data for the plurality of second sample periods, and may rearrange the obtained Doppler data based on the actual period.

Figure 17A:
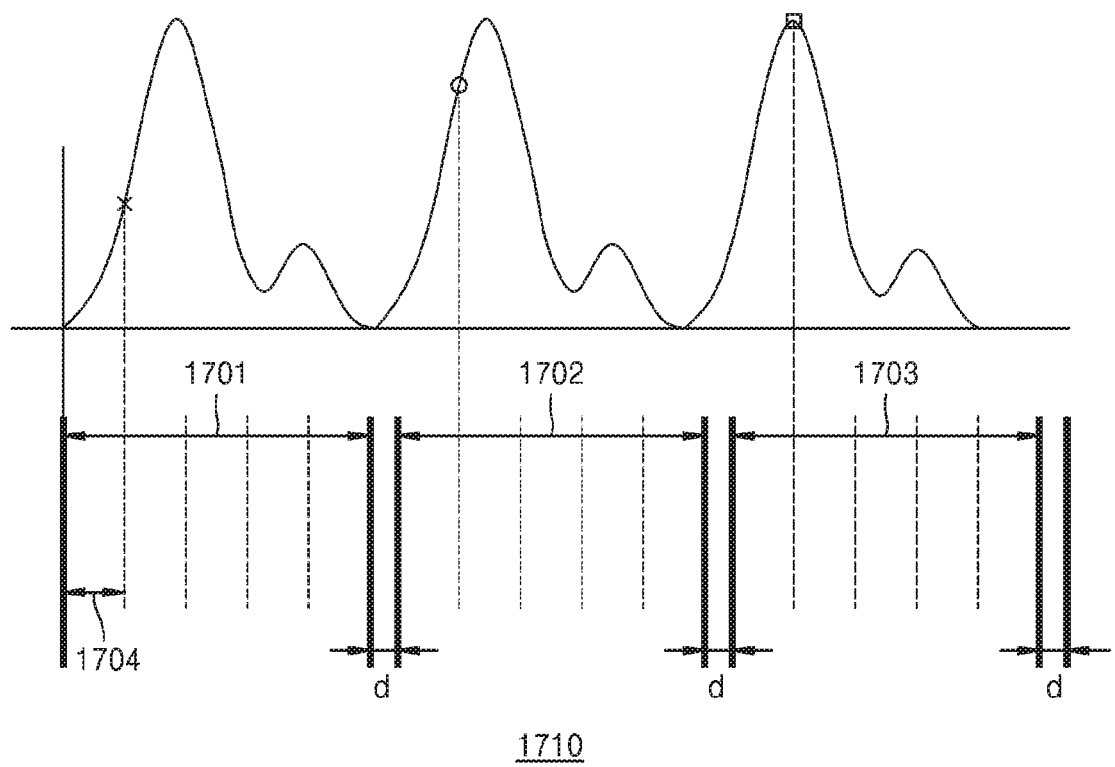
FIG. 17A is a diagram illustrating processes of obtaining Doppler data according to a first sample period, according to another embodiment.

FIG. 17A is a diagram illustrating processes of obtaining Doppler data according to a first sample period, according to another embodiment.

Referring to an image 1710 of FIG. 17A, the ultrasound imaging apparatus 1200 may obtain the Doppler data according to a first sample period 1704 during an actual first period 1701 of the heartbeat of the fetus. After obtaining the Doppler data in the first sample period 1704 during the actual first period 1701 of the heartbeat, the ultrasound imaging apparatus 1200 may delay a predetermined time period to obtain the Doppler data according to the first sample period 1704 during an actual second period 1702. In addition, after obtaining the Doppler data in the first sample period 1704 during the actual second period 1702 of the heartbeat, the ultrasound imaging apparatus 1200 may delay for a predetermined time period to obtain the Doppler data in the first sample period 1704 during an actual third period 1703.

Figure 17B:
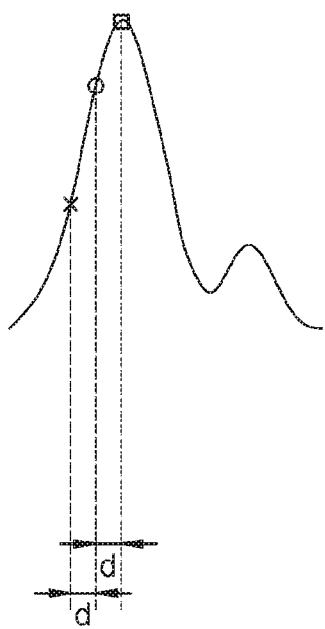
FIG. 17B is a diagram illustrating rearranging of obtained Doppler data, according to another embodiment.

FIG. 17B is a diagram illustrating rearranging of obtained Doppler data, according to another embodiment.

According to an image 1720 of FIG. 17B, the ultrasound imaging apparatus 1200 may rearrange the Doppler data sampled in the first sample period 1704 during the actual first period 1701 of the heartbeat of the fetus, the Doppler data sampled in the first sample period 1704 during the actual second period 1702 of the heartbeat of the fetus after delaying a predetermined time period, and the Doppler data sampled in the third sample period 1704 during the actual third period 1703 of the heartbeat of the fetus after delaying a predetermined time period, to overlap with one another within the actual first period 1701. The Doppler data obtained through overlapping may include more pieces of information about the heartbeat of the fetus than in the Doppler data sampled in the first sample period 1704 during the actual first period 1701.

Although the method of rearranging the Doppler data obtained according to the first sample period during the actual three periods of the heartbeat of the fetus is described with reference to FIGS. 17A and 17B, the ultrasound imaging apparatus 1200 may provide accurate Doppler data of the heartbeat of the fetus by obtaining the Doppler data for actual four or more periods and rearranging the Doppler data.

Figure 18A:
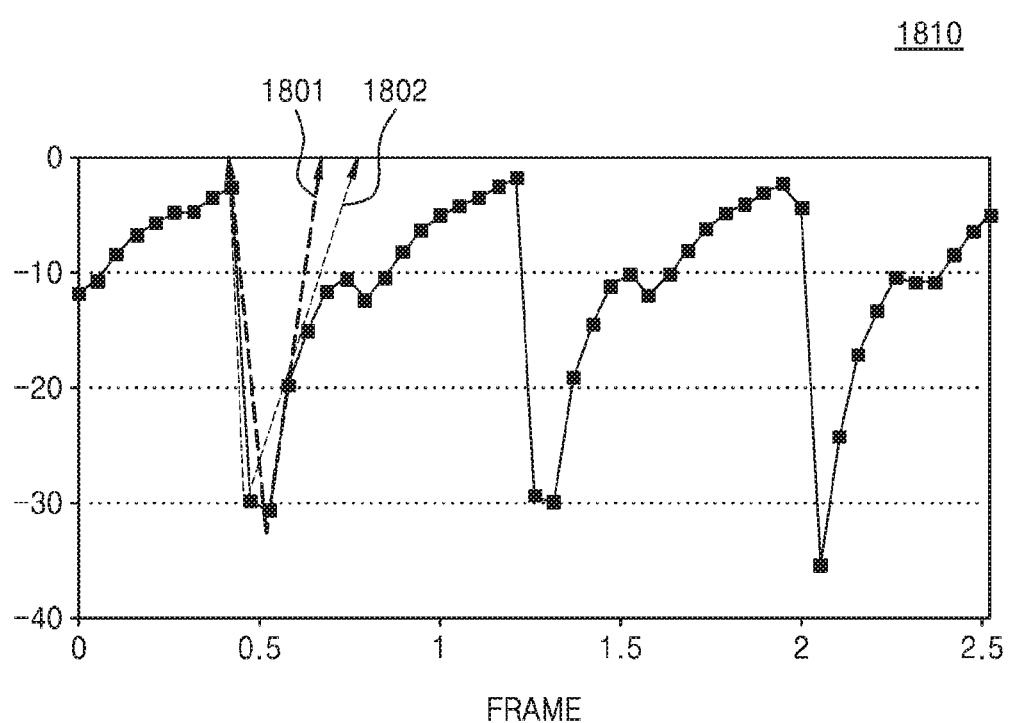
FIG. 18A is a diagram of Doppler data obtained according to a low sample rate, according to an embodiment.

FIG. 18A is a diagram of Doppler data obtained according to a low sample rate, according to an embodiment.

The ultrasound imaging apparatus 1200 may estimate fetal lung maturity by using the Doppler data. The ultrasound imaging apparatus 1200 measures values of parameters related to pulmonary blood flow index of the fetus from the Doppler data, and may estimate the fetal lung maturity based on the values of the parameters.

Here, the parameter may include an acceleration time representing a time period from a reference time to a point when the blood flow rate in the pulmonary trunk of the fetus is the highest according to contraction of heart, and an ejection time representing a time period from the reference time to a point when the blood flow rate in the pulmonary trunk of the fetus is changed according to relaxation of heart. The ultrasound imaging apparatus 1200 may estimate the fetal lung maturity based on a ratio of the acceleration time with respect to the ejection time.

As shown in a graph 1810 of FIG. 18A, in a case where a color Doppler image is used to measure a value about the acceleration time and a value about the ejection time, the ultrasound imaging apparatus 1200 may not identify an exact location of an inflection point in the Doppler data because the temporal resolution of the color Doppler image is low. Therefore, the ultrasound imaging apparatus 1200 may obtain the values about the acceleration time and the ejection time according to a first inflection point (1801), and may obtain values about the acceleration time and the ejection time according to a second inflection point (1802).

Figure 18B:
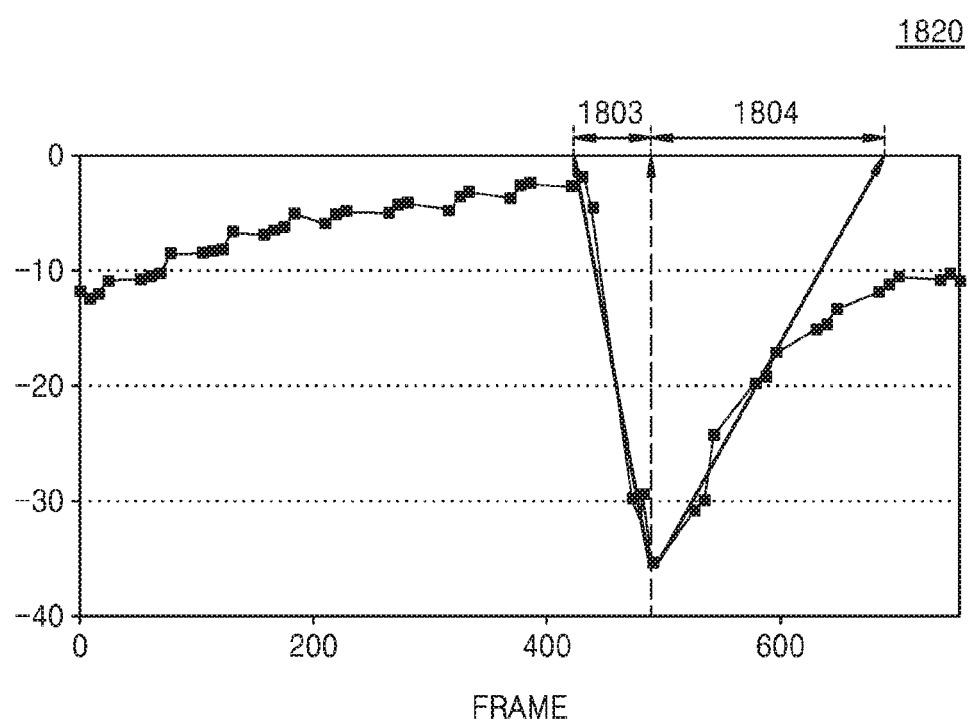
FIG. 18B is a diagram of Doppler data obtained by re-sampling Doppler data obtained according to a low sample rate, according to an embodiment.

FIG. 18B is a diagram of Doppler data obtained by re-sampling Doppler data obtained according to a low sample rate, according to an embodiment.

The ultrasound imaging apparatus 1200 may obtain Doppler data having high temporal resolution by obtaining the Doppler data of the object for a plurality of sample periods and rearranging the Doppler data according to an actual period of the object.

As shown in a graph 1820 of FIG. 18B, the ultrasound imaging apparatus 1200 may accurately identify location of an inflection point in the Doppler data, and may obtain a value 1803 of the acceleration time and a value 1804 of the ejection time.

The above-described ultrasound imaging apparatus may be implemented by using a hardware component, a software component, and/or a combination of a hardware component and a software component. For example, the apparatus and the component described in the exemplary embodiments may be implemented by using one or more general-purpose computers or a special-purpose computers such as, for example, a processor, a controller, an arithmetic logic unit (ALU), a digital signal processor, a microcomputer, a field programmable array (FPA), a programmable logic unit (PLU), a microprocessor, or any device that may execute an instruction and respond thereto.

A processor may execute an operating system (OS) and one or more software applications executed on the OS. Also, the processor may access, store, manipulate, process, and generate data in response to execution of software.

For convenience of understanding, though description has been made to the case where one processor is used, a person of ordinary skill in the art will understand that the processor may include a plurality of processing elements and/or processing elements having a plurality of types. For example, the processor may include a plurality of processors, or one processor and one controller. Also, the processor may include a different processing configuration such as a parallel processor.

Software may include a computer program, a code, an instruction, or a combination of one or more of these, and configure the processor to operate as desired, or instruct the processor independently or collectively.

Software and/or data may be embodied permanently or temporarily in a certain type of a machine, a component, a physical device, virtual equipment, a computer storage medium or device, or a transmitted signal wave in order to allow the processor to analyze the software and/or data, or to provide an instruction or data to the processor. Software may be distributed on a computer system connected via a network, and stored and executed in a distributed fashion. Software and data may be stored in one or more non-transitory computer-readable recording media.

The methods according to exemplary embodiments may be embodied in the form of program commands executable through various computer means, which may be recorded on a non-transitory computer-readable recording medium. The non-transitory computer-readable recording medium may include program commands, data files, and data structures either alone or in combination. The program commands recorded on the non-transitory computer-readable recording medium may be those that are especially designed and configured for the inventive concept, or may be those that are known and available to computer programmers skilled in the art.

Examples of the non-transitory computer-readable recording medium include magnetic recording media such as hard disks, floppy disks, and magnetic tapes, optical recording media such as CD-ROMs and DVDs, magneto-optical recording media such as floptical disks, and hardware devices such as ROMs, RAMs, and flash memories that are especially configured to store and execute program commands.

Examples of the program commands include machine language codes that may be generated by a compiler, and high-level language codes that may be executed by a computer by using an interpreter.

The above hardware device may be configured to operate as one or more software modules in order to perform an operation of an exemplary embodiment, and vice versa. Though the exemplary embodiments have been described by a limited number of exemplary embodiments and drawings, a person of ordinary skill in the art will make various modifications and changes from the above exemplary embodiments. For example, even when the described technologies are performed in an order different from the described method and/or components such as the described system, structure, apparatus, and circuit are coupled or combined in a form different from the described method, or replaced by other components or equivalents thereof, a proper result may be accomplished.

Therefore, the scope of the inventive concept should not be limited and determined by the described exemplary embodiments, but should be determined by not only the following claims but also equivalents thereof.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the inventive concept as defined by the following claims.

The invention claimed is:

1. An ultrasound imaging apparatus comprising:
a probe configured to receive ultrasound data from a lung of a fetus;
a processor configured to obtain Doppler data based on the ultrasound data, to measure a value about at least one parameter used to estimate lung maturity of the fetus, and to estimate the fetal lung maturity by using the measured value about the at least one parameter; and
a display configured to display a result of estimated lung maturity,
wherein the display is further configured to display a Doppler image of the fetus based on the Doppler data with at least one of estimated gestation of the fetal lung maturity and an index representing the estimated gestation of the fetal lung maturity,
wherein the display is further configured to display the estimated gestation of the fetal lung maturity as a quantitative value by numeral as a number of days,
wherein the at least one parameter comprises:
an acceleration time representing a time period from a reference time point to a point when a blood flow rate is the highest in the pulmonary trunk of the fetus according to contraction of the heart of the fetus; and
an ejection time representing a time period from the reference time point to a point when the blood flow rate in the pulmonary trunk of the fetus is changed according to relaxation of the heart of the fetus, and
wherein the processor is further configured to calculate values about the acceleration time and the ejection time based on the Doppler data including the blood flow rate in the pulmonary trunk of the fetus to estimate the fetal lung maturity.

2. The ultrasound imaging apparatus of claim 1, wherein the at least one parameter is a parameter related to a pulmonary blood flow index of the fetus.

3. The ultrasound imaging apparatus of claim 1, wherein the Doppler data is a Doppler waveform having periods and representing a blood flow rate in the pulmonary trunk of the fetus.

4. The ultrasound imaging apparatus of claim 1, wherein the processor estimates the fetal lung maturity by using the measured value about the at least one parameter and a standard value about the at least one parameter of a plurality of fetuses according to gestation growth.

5. The ultrasound imaging apparatus of claim 4, wherein the processor compares the measured value about the at least one parameter with the standard value, and estimates gestation of the fetal lung maturity according to a comparison result.

6. The ultrasound imaging apparatus of claim 1, wherein the display displays the measured value about the at least one parameter and a standard value of the at least one parameter according to the estimated gestation of the fetal lung maturity.

7. The ultrasound imaging apparatus of claim 1, wherein the processor determines safety of the fetal lung maturity based on at least one of the estimated gestation of the fetal lung maturity according to gestation growth of the fetus and the index representing the estimated gestation of the fetal lung maturity, and the display displays a result of determination of the safety of the fetal lung maturity.

8. The ultrasound imaging apparatus of claim 1, further comprising a user interface configured to receive the at least one parameter used to estimate the fetal lung maturity, wherein the processor estimates the fetal lung maturity based on an input of the at least one parameter.

* * * * *